(12) United States Patent
Frechet et al.

(10) Patent No.: US 10,995,156 B2
(45) Date of Patent: *May 4, 2021

(54) ACID-DEGRADABLE AND BIOERODIBLE MODIFIED POLYHYDROXYLATED MATERIALS

(71) Applicant: The Regents of the University of California, Oakland, CA (US)

(72) Inventors: Jean M. J. Frechet, Oakland, CA (US); Eric M. Bachelder, Dublin, OH (US); Tristan T. Beaudette, San Francisco, CA (US); Kyle E. Broaders, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/474,827

(22) Filed: Mar. 30, 2017

(65) Prior Publication Data

US 2017/0298151 A1 Oct. 19, 2017

Related U.S. Application Data

(63) Continuation of application No. 12/987,679, filed on Jan. 10, 2011, now Pat. No. 9,644,039, which is a
(Continued)

(51) Int. Cl.
| | | |
|---|---|---|
| *C08B 37/00* | (2006.01) | |
| *A61K 9/16* | (2006.01) | |
| *A61L 17/10* | (2006.01) | |
| *A61L 17/14* | (2006.01) | |
| *A61L 27/14* | (2006.01) | |
| *A61L 27/34* | (2006.01) | |
| *A61L 27/58* | (2006.01) | |
| *A61L 31/10* | (2006.01) | |
| *A61L 31/14* | (2006.01) | |

(Continued)

(52) U.S. Cl.
CPC ............ *C08B 37/0006* (2013.01); *A61K 9/00* (2013.01); *A61K 9/1652* (2013.01); *A61K 38/02* (2013.01); *A61K 38/16* (2013.01); *A61K 39/00* (2013.01); *A61K 39/0011* (2013.01); *A61K 39/385* (2013.01); *A61K 39/395* (2013.01); *A61K 45/06* (2013.01); *A61K 47/50* (2017.08); *A61K 47/6939* (2017.08); *A61L 17/10* (2013.01); *A61L 17/145* (2013.01); *A61L 27/14* (2013.01); *A61L 27/34* (2013.01); *A61L 27/58* (2013.01); *A61L 31/10* (2013.01); *A61L 31/148* (2013.01); *C08B 30/18* (2013.01); *C08B 37/0021* (2013.01); *C08B 37/14* (2013.01); *C08F 8/00* (2013.01); *C08F 8/02* (2013.01); *C08F 8/48* (2013.01); *C08F 16/06* (2013.01); *C08F 216/38* (2013.01); *C08L 1/02* (2013.01); *C08L 1/08* (2013.01); *C08L 3/02* (2013.01); *C08L 5/00* (2013.01); *C08L 5/02* (2013.01); *C08L 5/06* (2013.01); *C08L 101/02* (2013.01); *C09D 129/14* (2013.01); *A61K 2039/55555* (2013.01); *A61K 2039/55561* (2013.01); *B82Y 5/00* (2013.01)

(58) Field of Classification Search
CPC ........ A61K 38/02; A61K 38/16; A61K 39/00; A61K 39/0011; A61K 39/385; A61K 39/395; A61K 45/06; A61K 47/50; A61K 47/6939; A61K 9/00; A61K 9/1652; A61L 17/10

See application file for complete search history.

(56) References Cited

U.S. PATENT DOCUMENTS

| | | |
|---|---|---|
| 5,191,015 A | 3/1993 | Sheppard et al. |
| 6,333,051 B1 | 12/2001 | Kabanov et al. |

(Continued)

FOREIGN PATENT DOCUMENTS

| | | |
|---|---|---|
| JP | 2001515924 A | 9/2001 |
| JP | 4036882 B2 | 1/2008 |

OTHER PUBLICATIONS

Gillies Acetals as pH-sensitive linkages Bioconjugate Chem p. 1254 (Year: 2004).*

(Continued)

*Primary Examiner* — Matthew P Coughlin
*Assistant Examiner* — Thurman Wheeler
(74) *Attorney, Agent, or Firm* — Mintz Levin Cohn Ferris Glovsky and Popeo, P.C.

(57) ABSTRACT

Compositions and methods of making a modified polyhydroxylated polymer comprising a polyhydroxylated polymer having reversibly modified hydroxyl groups, whereby the hydroxyl groups are modified by an acid-catalyzed reaction between a polydroxylated polymer and a reagent such as acetals, aldehydes, vinyl ethers and ketones such that the modified polyhydroxylated polymers become insoluble in water but freely soluble in common organic solvents allowing for the facile preparation of acid-sensitive materials. Materials made from these polymers can be made to degrade in a pH-dependent manner. Both hydrophobic and hydrophilic cargoes were successfully loaded into particles made from the present polymers using single and double emulsion techniques, respectively. Due to its ease of preparation, processability, pH-sensitivity, and biocompatibility, of the present modified polyhydroxylated polymers should find use in numerous drug delivery applications.

22 Claims, 23 Drawing Sheets

Specification includes a Sequence Listing.

Related U.S. Application Data continuation of application No. PCT/US2009/049415, filed on Jul. 1, 2009.

(60) Provisional application No. 61/079,091, filed on Jul. 8, 2008.

(51) Int. Cl.

| | |
|---|---|
| C08B 30/18 | (2006.01) |
| C08B 37/02 | (2006.01) |
| C08L 1/02 | (2006.01) |
| C08L 1/08 | (2006.01) |
| C08L 3/02 | (2006.01) |
| C08L 5/00 | (2006.01) |
| C08L 5/02 | (2006.01) |
| C08L 5/06 | (2006.01) |
| A61K 9/00 | (2006.01) |
| A61K 45/06 | (2006.01) |
| C08B 37/14 | (2006.01) |
| A61K 47/69 | (2017.01) |
| C09D 129/14 | (2006.01) |
| A61K 39/00 | (2006.01) |
| A61K 39/385 | (2006.01) |
| C08L 101/02 | (2006.01) |
| A61K 47/50 | (2017.01) |
| C08F 216/38 | (2006.01) |
| C08F 8/02 | (2006.01) |
| C08F 8/48 | (2006.01) |
| C08F 8/00 | (2006.01) |
| A61K 38/02 | (2006.01) |
| A61K 38/16 | (2006.01) |
| A61K 39/395 | (2006.01) |
| C08F 16/06 | (2006.01) |
| B82Y 5/00 | (2011.01) |

(56) References Cited

U.S. PATENT DOCUMENTS

| | | | |
|---|---|---|---|
| 7,056,901 B2 | 6/2006 | Frechet et al. | |
| 7,307,065 B2 | 12/2007 | Schinazi et al. | |
| 7,683,041 B2 | 3/2010 | Frechet et al. | |
| 8,137,700 B2 | 3/2012 | Frechet et al. | |
| 2004/0254141 A1 | 12/2004 | Schinazi et al. | |
| 2005/0261490 A1 | 11/2005 | Perplies et al. | |

OTHER PUBLICATIONS

Paramonov Fully acid-degradable biocompatible polyacetal Bioconjugate Chem. p. 911 (Year: 2008).*
Bystricky (Candida albicans mannan-protein conjugate Immunology Letters p. 251 (Year: 2003).*
Coombes Biodegrad. polym. micropart. for drug del. Biomaterials, p. 1153 (Year: 1997).*
Darcy, Journal of Chemical Education, p. 1090 (Year: 1990).*
Akinc et al., "Parallel synthesis and biophysical characterization of a degradable polymer library for gene delivery," J. Am. Chem. Soc., 125, pp. 5316-5323 (2003).
Bachelder et al., "Acetal-Derivatized Dextran: An Acid-Responsive Biodegradable Material for Therapeutic Applications," J. Am. Chem. Soc., 130, pp. 10494-10495 (2008).
Bachelder et al., "Acid-degradable polyurethane particles for protein-based vaccines: biological evaluation and in vitro analysis of particle degradation products," Mol. Pharmaceutics, 5(5), pp. 876-884 (2008).
Broaders et al., "Acetalated dextran is a chemically and biologically tunable material for particulate immunotherapy," PNAS, 106(14), pp. 5497-5502 (Apr. 7, 2009).
Bystricky et al., "Candida albicans mannan-protein conjugate as vaccine candidate," Immunology Letters, 85, pp. 251-255 (2003).
Bystricky et al., "Conjugation of yeast mannans with protein employing cyanopyridinium agent (CDAP)—an effective route of antifungal vaccine preparation," Glycoconjugate Journal, 17, pp. 677-680 (2000).
Gillies et al., "Acetals as pH-sensitive linkages for drug delivery," Bioconjugate Chem., 15, pp. 1254-1263 (2004).
Lynn and Langer, "Degradable Poly(ß-amino esters): Synthesis, Characterization, and Self-Assembly with Plasmid DNA," J. Am. Chem. Soc., 122, pp. 10761-10768 (2000).
Paramonov et al., "Fully acid-degradable biocompatible polyacetal microparticles for drug delivery," Bioconjugate Chem., 19, pp. 911-919 (2008).
Ruckenstein et al., "A Novel Breakable Cross-Linker and pH-Responsive Star-Shaped and Gel Polymers," Macromolecules, 32, 3979-3983 (1997).
Van Dijk-Wolthuis et al., "Degradation and Release Behavior of Dextran-Based Hydrogels," Macromolecules, 30, pp. 4639-4645 (1997).
Van Dijk-Wolthuis et al., "Degradation and Release Behavoir of Dextran-Based Hydrogels," Macromolecules, 30, pp. 4639-4645 (1997).
Witschi et al., "In vitro evaluation of microparticles and polymer gels for use as nasal platforms for protein delivery," Pharmaceutical Research, 16(3), pp. 382-390 (1999).

* cited by examiner

Mannan:

Polyvinyl alcohol:

Figure 12: Particles Prepared from Ac-Dex
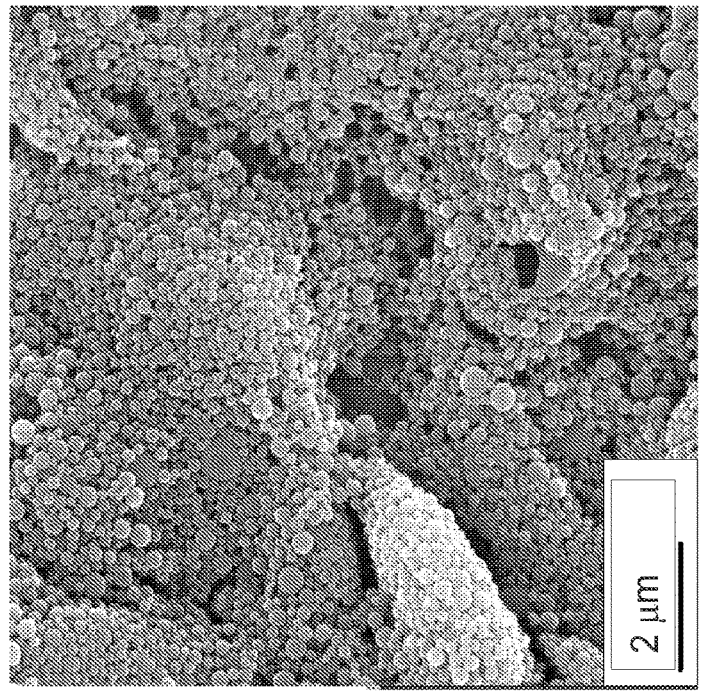
Encapsulated Cargoes:
- Ovalbumin (protein)
- Doxorubicin (chemotherapeutic)
- pyrene (hydrophobic model drug)
- FITC-Dextran (hydrophilic model drug)
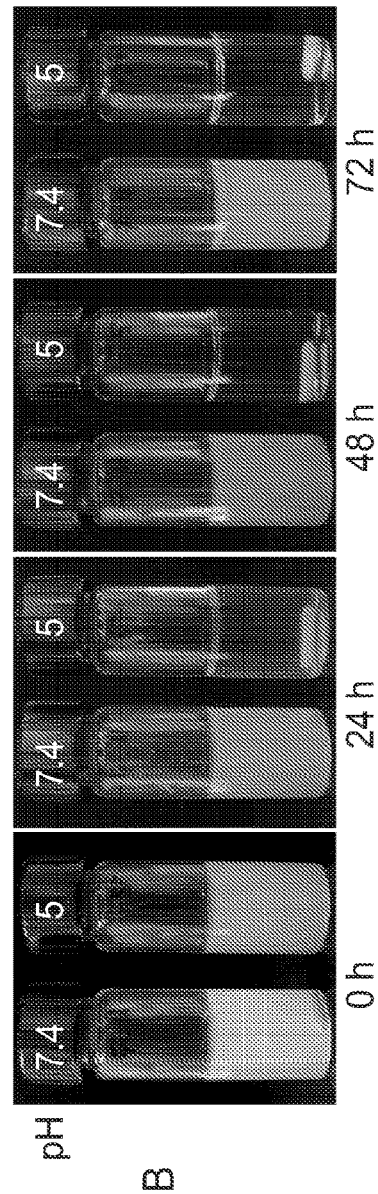

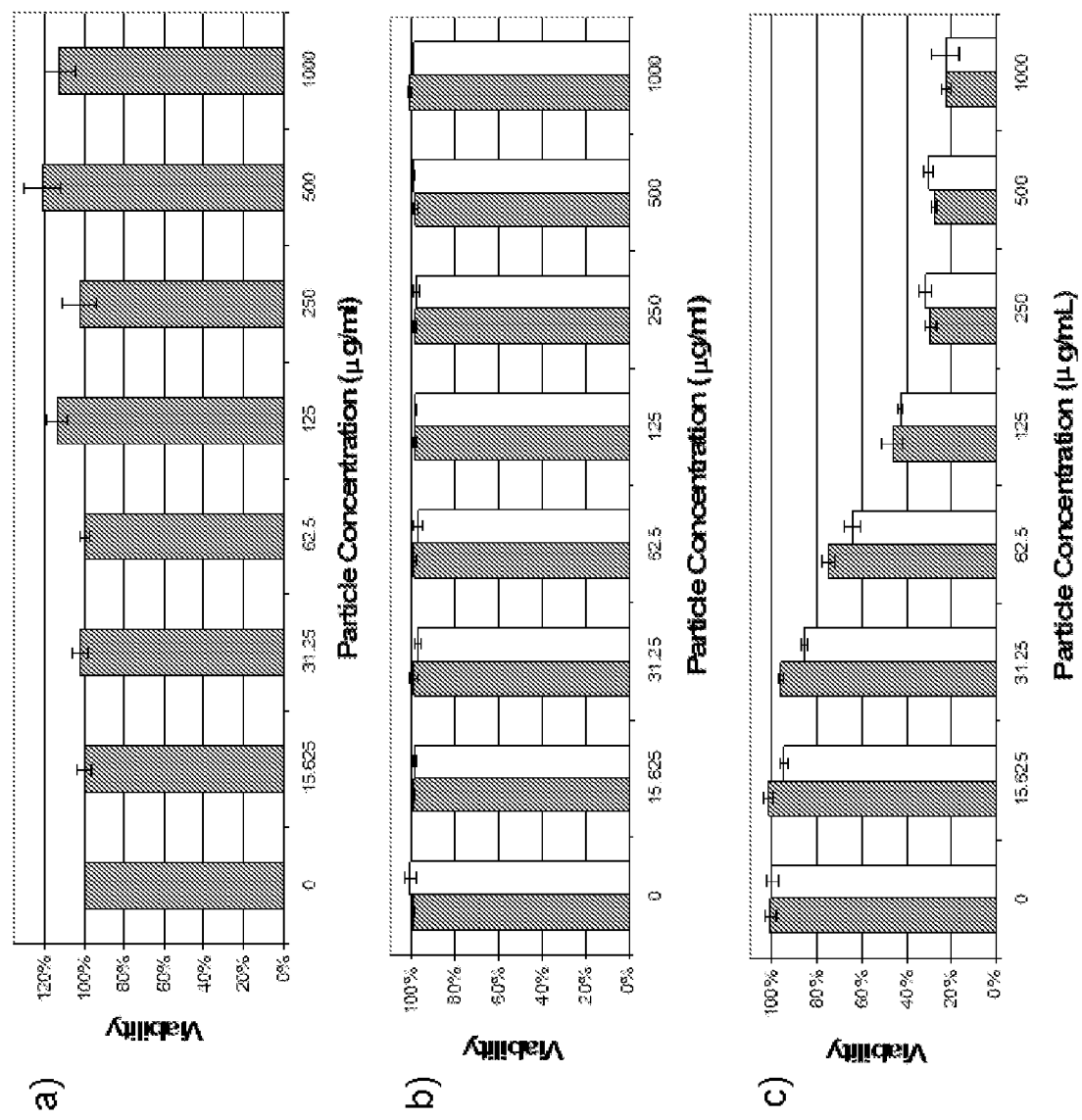

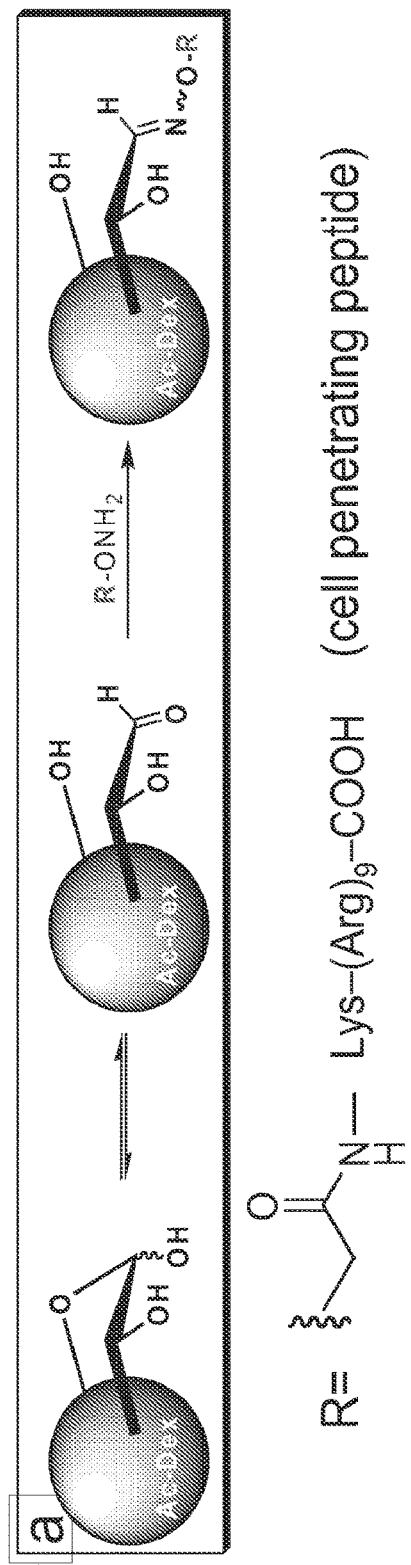
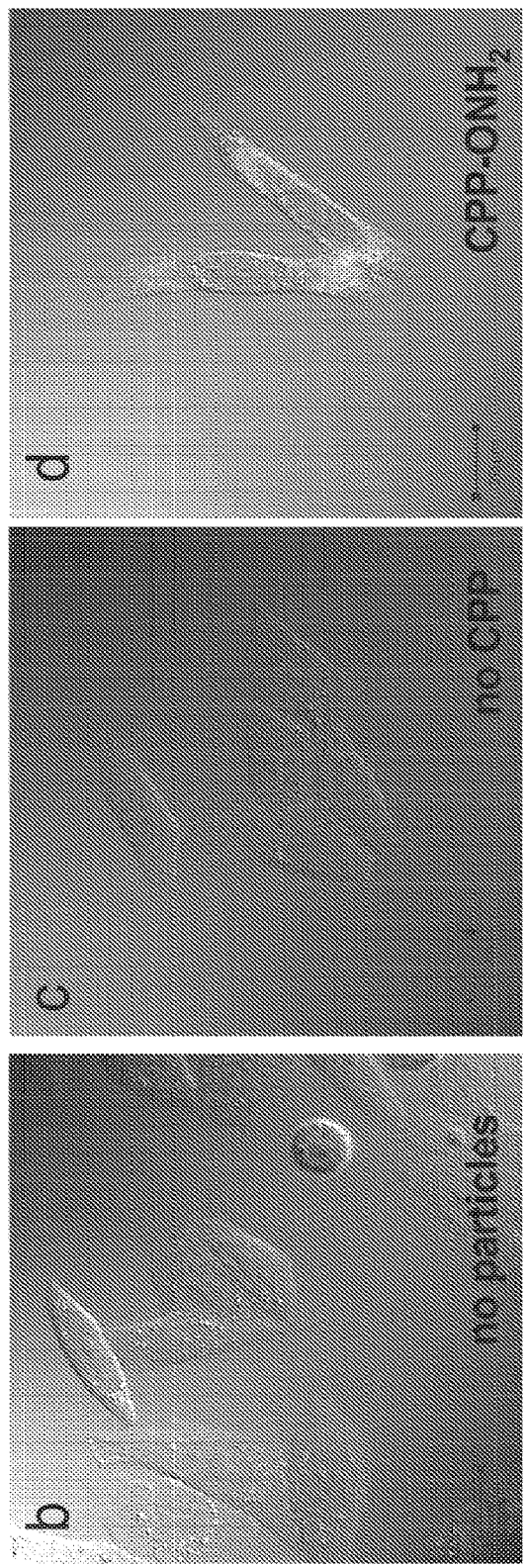
Figure 21

SEQUENCE LISTING

```
<160> NUMBER OF SEQ ID NOS: 8

<210> SEQ ID NO 1
<211> LENGTH: 16
<212> TYPE: PRT
<213> ORGANISM: Artificial
<220> FEATURE:
<223> OTHER INFORMATION: SV40 large T antigen nuclear localization
      signal

<400> SEQUENCE: 1

Pro Pro Lys Lys Lys Arg Lys Val Pro Pro Lys Lys Lys Arg Lys Val
1               5                   10                  15

<210> SEQ ID NO 2
<211> LENGTH: 11
<212> TYPE: PRT
<213> ORGANISM: Artificial
<220> FEATURE:
<223> OTHER INFORMATION: HIV TAT protein  nuclear localization signal
      peptide

<400> SEQUENCE: 2

Tyr Gly Arg Lys Lys Arg Arg Gln Arg Arg Arg
1               5                   10

<210> SEQ ID NO 3
<211> LENGTH: 19
<212> TYPE: PRT
<213> ORGANISM: Artificial
<220> FEATURE:
<223> OTHER INFORMATION: endoplasmic reticulum-targeting signal peptide

<400> SEQUENCE: 3

Lys Asp Glu Leu Ala Lys Asp Glu Leu Ala Lys Asp Glu Leu Ala Lys
1               5                   10                  15

Asp Glu Leu

<210> SEQ ID NO 4
<211> LENGTH: 28
```

```
<212> TYPE: PRT
<213> ORGANISM: Artificial
<220> FEATURE:
<223> OTHER INFORMATION: cytochrome C oxidase mitochondrial-targeting
      signal peptide

<400> SEQUENCE: 4

Ser Val Thr Thr Pro Leu Leu Leu Arg Gly Leu Thr Gly Ser Ala Arg
1               5                   10                  15

Arg Leu Pro Val Pro Arg Ala Lys Ile His Ser Leu
            20                  25

<210> SEQ ID NO 5
<211> LENGTH: 16
<212> TYPE: PRT
<213> ORGANISM: Artificial
<220> FEATURE:
<223> OTHER INFORMATION: PTS1 peroxisome-targeting signal peptide

<400> SEQUENCE: 5

Ser Lys Leu Ala Ser Lys Leu Ala Ser Lys Leu Ala Ser Lys Leu Ala
1               5                   10                  15

<210> SEQ ID NO 6
<211> LENGTH: 19
<212> TYPE: PRT
<213> ORGANISM: Artificial
<220> FEATURE:
<223> OTHER INFORMATION: cell membrane-targeting signal peptide

<400> SEQUENCE: 6

Lys Leu Asn Pro Pro Asp Glu Ser Gly Pro Cys Met Ser Cys Lys Cys
1               5                   10                  15

Val Leu Ser

<210> SEQ ID NO 7
<211> LENGTH: 20
<212> TYPE: PRT
<213> ORGANISM: Artificial
<220> FEATURE:
<223> OTHER INFORMATION: GAP-43 cell membrane-targeting signal peptide

<400> SEQUENCE: 7

Met Leu Cys Cys Met Arg Arg Thr Lys Gln Val Glu Lys Asn Asp Glu
1               5                   10                  15

Asp Gln Lys Ile
            20

<210> SEQ ID NO 8
<211> LENGTH: 8
<212> TYPE: PRT
<213> ORGANISM: Artificial
<220> FEATURE:
<223> OTHER INFORMATION: Ovalbumin derived peptide displayed by antigen
      presenting cells

<400> SEQUENCE: 8

Ser Ile Ile Asn Phe Glu Lys Leu
1               5
```

ACID-DEGRADABLE AND BIOERODIBLE MODIFIED POLYHYDROXYLATED MATERIALS

CROSS-REFERENCE TO RELATED APPLICATIONS

This application is a continuation of U.S. application Ser. No. 12/987,679, filed on Jan. 10, 2011, which claims priority to International Application No. PCT/US2009/049415, filed on Jul. 1, 2009 and U.S. Provisional Patent Application No. 61/079,091, filed on Jul. 8, 2008, both of which are hereby incorporated by reference in their entirety.

This application is related to and incorporates by reference U.S. Provisional Patent Application No. 60/798,177, filed on May 5, 2006. This application is also related to and incorporates by reference co-pending divisional U.S. patent application Ser. No. 11/388,924, filed on Mar. 28, 2006.

STATEMENT OF GOVERNMENT SUPPORT

This invention was made during work partially supported by National Institutes of Health under Grant RO1GM44885-16 and Grant RO1 EB005824 and the U.S. Department of Energy under Contract No. DE-AC02-05CH11231. The government has certain rights in this invention.

REFERENCE TO SEQUENCE LISTING

This application also incorporates by reference the attached sequence listing containing cellular targeting sequences in electronic and paper form, hereby certified as identical copies.

BACKGROUND OF THE INVENTION

Field of the Invention

This invention generally relates to the field of acid-degradable and bioerodible materials and polymers for use in delivery of bioactive materials such as antigens, DNA and other therapeutics or as bulk materials such as sutures, scaffolds, and implants.

Description of the Related Art

Polyesters, polyorthoesters, and polyanhydrides are widely used materials for biomedical applications due to their biodegradability, biocompatibility and processability (Yolles, S.; Leafe, T. D.; Meyer, F. J., *J. Pharm. Sci.* 1975, 64, 115-6; Heller, J., *Ann. N. Y. Acad. Sci.* 1985, 446, 51-66; Rosen, H. B.; Chang, J.; Wnek, G. E.; Linhardt, R. J.; Langer, R., *Biomaterials* 1983, 4, 131-3). Microparticles made from these polymers have been used as carriers for vaccine applications, gene delivery and chemotherapeutic agents. (Solbrig, C. M.; Saucier-Sawyer, J. K.; Cody, V.; Saltzman, W. M.; Hanlon, D. J., *Mol. Pharm.* 2007, 4, 47-57; Gvili, K.; Benny, O.; Danino, D.; Machluf, M., *Biopolymers* 2007, 85, 379-91; Sengupta, S.; Eavarone, D.; Capila, I.; Zhao, G. L.; Watson, N.; Kiziltepe, T.; Sasisekharan, R., *Nature* 2005, 436, 568-572). The encapsulated cargo is typically released over the course of several months via surface erosion and the slow degradation of the polymer. (Matsumoto, A.; Matsukawa, Y.; Suzuki, T.; Yoshino, H., *J. Control Release* 2005, 106, 172-80).

For many drug delivery applications, it is desirable to release therapeutic agents under mildly acidic conditions, which can be found for example in sites of inflammation, lysosomal compartments, or tumor tissue. ((a) Sun-Wada, G. H.; Wada, Y.; Futai, M., *Cell Struct. Funct.* 2003, 28, 455-63 (b) Helmlinger, G.; Sckell, A.; Dellian, M.; Forbes, N. S.; Jain, R. K., *Clin. Cancer Res.* 2002, 8, 1284-91) Acid-sensitive liposomes, micelles and hydrogels ((a) Sawant, R. M.; Hurley, J. P.; Salmaso, S.; Kale, A.; Tolcheva, E.; Levchenko, T. S.; Torchilin, V. P., *Bioconjug Chem* 2006, 17, 943-9 (b) Mandracchia, D.; Pitarresi, G.; Palumbo, F. S.; Carlisi, B.; Giammona, G., *Biomacromolecules* 2004, 5, 1973-82 (c) Murthy, N.; Thng, Y. X.; Schuck, S.; Xu, M. C.; Frechet, J. M. J., *J. Am. Chem. Soc.* 2002, 124, 12398-12399) have previously been developed, but few easily-prepared polymeric materials exist that combine acid-sensitivity and biodegradability.

Poly($\beta$-amino esters), which are protonated and thus become soluble at lower pH (Little, S. R.; Lynn, D. M.; Ge, Q.; Anderson, D. G.; Puram, S. V.; Chen, J.; Eisen, H. N.; Langer, R., *Proc. Natl. Acad. Sci. U.S.A* 2004, 101, 9534-9), constitute one such material. However, these polymers become polycationic under acidic conditions and must be blended with biocompatible polyesters to reduce their toxicity (Little, S. R.; Lynn, D. M.; Puram, S. V.; Langer, R., *J. Control Release* 2005, 107, 449-62).

Currently there is no system with the flexibility and biocompatibility of polyester materials, but with the additional benefit of a change in rate of payload release that is sensitive to physiologically relevant acidic conditions.

BRIEF SUMMARY OF THE INVENTION

The present invention is directed to bioerodible modified polyhydroxylated polymers for application in the delivery of proteins, vaccines, drugs (such as the anticancer drugs cisplatin, paclitaxel or taxotere), and other bioactive materials. In one embodiment, the modified polyhydroxylated polymer comprising a polyhydroxylated polymer with reversibly modified hydroxyl groups, wherein the hydroxyl groups are modified by a one-step reaction to feature a functional group selected from the group consisting of acetals, aromatic acetals, and ketals.

In one preferred embodiment, the hydroxyl groups in the polyhydroxylated polymers are modified, thereby rendering the modified polyhydroxylated polymer acid-degradable, pH sensitive and insoluble in water.

In a preferred embodiment, the modified polyhydroxylated polymers are also acid-degradable comprising acid-degradable modified polyhydroxylated polymers that are designed to deliver bioactive materials. In one embodiment, the modified polyhydroxylated polymers deliver bioactive materials upon hydrolysis of an acetal or ketal linkage at pH 5 to pH 7.4. In one embodiment, the polymer compositions are made using polyhydroxylated polymers resulting in modified polyhydroxylated polymers containing an acid-degradable linkage, which hydrolyzes to release and deliver bioactive material. In another embodiment, the modified polyhydroxylated polymers are bioerodible whereby degradation of the polymers allows for slow release of any bioactive material to be delivered.

The polymers may be processed to form particles, bulk materials or implants for the pH dependent controlled release of small drug or biotherapeutics. These polymers could also be used as vehicles for drug conjugation or complexation designed to release their drug at mild pH values or scaffolds for tissue engineering purposes.

The polymers of the current invention are designed to degrade into natural polyhydroxylated products, releasing their contents in response to the mildly acidic conditions found in lysosomes, tumors, and inflammatory tissues. In one embodiment, the present polymers will hydrolyze at a preferred pH range of 4.5 to 6.8, more preferably pH 5.0 to 6.0. Preferably, the polymers will completely hydrolyze within 24 hours at pH 5.0, or conditions such as in the lysosome, and release their encapsulated or bound contents after entering a cell.

In one embodiment, the polyhydroxylated polymers are preformed natural polymers or hydroxyl-containing polymers including but not limited to, multiply-hydroxylated polymers, polysaccharides, carbohydrates, polyols, polyvinyl alcohol, poly amino acids such as polyserine, and other polymers such as 2-(hydroxyethyl)methacrylate.

In one embodiment, the polysaccharides that can be used include but are not limited to, dextran, mannan, pullulan, maltodextrin, starches, cellulose and cellulose derivatives, gums (e.g., xanthan, locust bean, etc.), and pectin. In one embodiment, the polysaccharides are dextran or mannan.

In another embodiment, the modified polysaccharides have pendant acetals, thus providing acetal-derivatized polysaccharides. In one embodiment, the modified polyhydroxylated polymers are acetal-derivatized dextran, acetal-derivatized mannan or acetal-derivatized polyvinyl alcohols.

In one embodiment, the reversible modification of the polyhydroxylated polymer to produce the present acid-degradable and bioerodible modified polyhydroxylated polymers is performed in a one-step modification process. The one-step reversible modification of the hydroxyl groups can be carried out to provide modified hydroxyl groups, wherein at least 20%, 25%, 30%, 40%, 50%, 60%, 70%, 75%, 80%, 85%, 90%, 95%, 98%, 99% or 100% of the hydroxyl groups in the polymer are modified.

In one embodiment, polyhydroxylated polymers are prepared and reacted with a functionalizing group and result in a variety of pH sensitive and functionalized polyhydroxylated polymers with different solubilities.

This class of polymers are simple to prepare and completely degradable. Select polymers were characterized. The degradation of these polymers into small molecules was monitored at pH 7.4 and pH 5 over time along with methods of controlling the rate of degradation, thus making these polymers promising candidates for drug delivery systems.

A method of preparing a modified polyhydroxylated acid-degradable composition for delivering a bioactive material to a cell, comprising the steps of (a) preparing a mixture which contains a polyhydroxylated polymer and a functional group, wherein a one-step reaction provides a modified polyhydroxylated polymer having modified hydroxyl groups containing an acid-degradable linkage; (b) forming particles of the polymer in the presence of a bioactive material; and (c) recovering the resulting polymer particles having bioactive material bound or entrapped thereto.

BRIEF DESCRIPTION OF THE DRAWINGS

FIG. 12B shows time-lapse photos of Ac-DEX particles under physiological or acidic conditions FIG. 13 dissolution half life at pH 5 vs dextran reaction time.

FIG. 21. Particles made from Ac-DEXwere (a) modified at their reducing ends through oxime linkages using cell penetrating peptides (CPP) containing an aminoxy group. HeLa cells (b) were incubated with fluorescently labeled Ac-DEX particles that were either (c) unmodified or (d)

Figure 1:
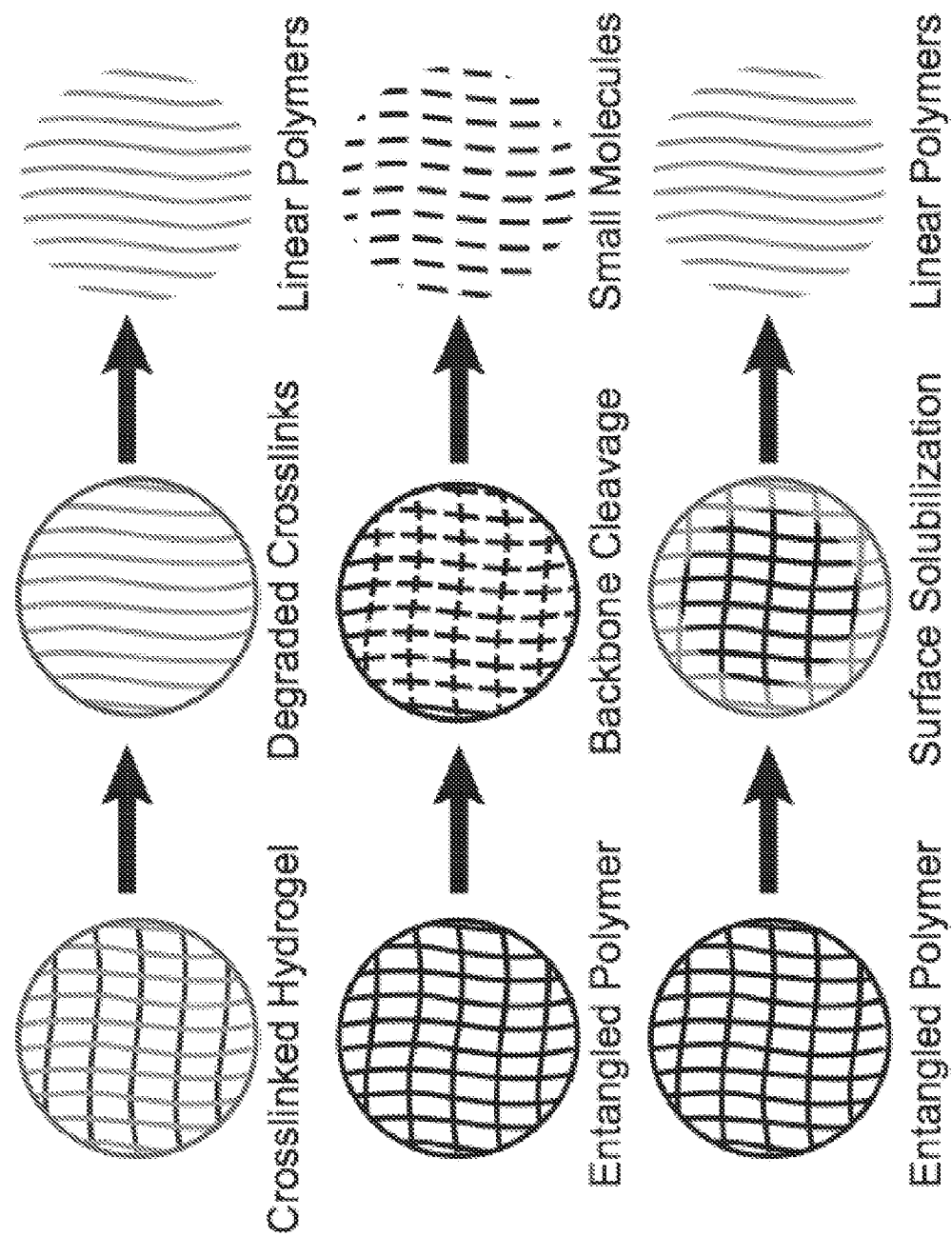
FIG. 1 shows previous acid-degradable systems (top and middle) compared to the present system (bottom).

modified with CPP groups. Modification with CPPs led to significantly enhanced uptake of particles relative to unmodified particles.

DESCRIPTION OF THE PREFERRED EMBODIMENT

Definitions

The term "bioactive material" herein refers to a composition having a physiological effect on a cell, such as a protein, antigen, polypeptide, polynucleotide, an enzyme or other organic molecule, for example, drugs or chemotherapeutics.

The terms "nucleotide", "oligonucleotide", and "polynucleotide" herein refer to single- or multi-stranded deoxyribonucleotides (DNA), single- or multi-stranded ribonucleotides (RNA), or single- or multi-stranded peptide nucleic acids (PNA).

The term "acetal" herein refers to a geminal diether in which both ether oxygens are bound to the same carbon.

The term "aryl" herein refers to a homocyclic aromatic, whether or not fused, having 6 to 12 carbon atoms optionally substituted with one to three substituents, wherein said substituents are preferably N or O, or unsubstituted.

The term "alkyl" herein refers to an aliphatic linear or branched chain univalent groups of the general formula $C_nH_{2n+1}$ derived from aliphatic hydrocarbons such as methyl $CH_3$, ethyl $C_2H_5$, propyl $C_3H_7$, 2-methyl propyl $C_4H_{11}$, and the like or cyclic aliphatic univalent groups of the general formula $C_nH_{2-1}$ derived from cyclic aliphatic hydrocarbons, such as cyclypropyl $C_3H_5$, cyclopentyl $C_5H_9$ and the like, where n is between 2 and 20.

The term "loading" herein refers to the amount of bioactive material that is encapsulated per milligram of the drug delivery systems. This may be expressed in terms of μg material/mg drug delivery system, on average, based on the starting bioactive material/polymers ratio.

The term "loading efficiency" herein refers to the percentage of the starting amount of bioactive material that is actually encapsulated.

The term "ketal" herein refers to an acetal in which the central carbon bound to two oxygen atoms is bound to two alkyl groups.

The terms "d", "min", "s" and "rt" used herein refer to days, minutes, seconds, and room temperature, respectively.

Introduction

In one embodiment, the present invention provides a modified polyhydroxylated polymer comprising a polyhydroxylated polymer having reversibly modified hydroxyl groups, wherein the hydroxyl groups are modified by a one-step reaction to feature a functional group selected from the group consisting of acetals, aromatic acetals, ketals.

In one preferred embodiment, the hydroxyl groups in the polyhydroxylated polymers are modified, thereby rendering the modified polyhydroxylated polymer acid degradable, pH sensitive and insoluble in water.

Thus, the present invention describes a system with the flexibility and biocompatibility of polyester materials, but with the additional benefit of a change in rate of hydrolysis or degradation that is sensitive to physiologically relevant acidic conditions. Thus in one embodiment, a solubility switching mechanism is used in which a biocompatible, water-soluble (polyhydroxylated) polymer may be reversibly modified to make it insoluble in water, but soluble in organic solvents. Materials made from the modified polyhydroxylated polymer could then be degraded under the specific conditions that reverse the original modification.

In one embodiment, hydroxyl groups displayed on the polyhydroxylated polymer backbone are modified to display a functional group having an acetal or ketal linkage therein. This group is designed to remain largely stable in plasma at neutral physiological pH (about 7.4), but degrade intracellularly by hydrolysis in the more acidic environment of the endosome or lysosome (about pH 5.0-6.0). The modified polyhydroxylated polymers exhibit hydrolysis and degradation, whereby the resulting degradation products are the polyhydroxylated polymer and the small molecule byproducts.

In a preferred embodiment, the modified polyhydroxylated polymers are processed to deliver a bioactive material. In a preferred embodiment, polymer particles hydrolyze under acidic conditions and release the bioactive material in response to the mildly acidic conditions, found in the body such as in tumors, inflammatory tissues and in cellular compartments such as lysosomes and phagolysosomes of antigen presenting cells.

In a preferred embodiment, the bioactive material includes but is not limited to, antigens, proteins, polynucleotides, polypeptides, peptoids, small drug molecules and other bioactive material.

A. Polyhydroxylated Polymers

In one embodiment, the polyhydroxylated polymers are preformed natural polymers or hydroxyl-containing polymers including but not limited to, multiply-hydroxylated polymers, polysaccharides, carbohydrates, polyols, polyvinyl alcohol, poly amino acids such as polyserine, and other polymers such as 2-(hydroxyethyl)methacrylate.

In one embodiment, the polysaccharides that can be used include but are not limited to, dextran, mannan, pullulan, maltodextrin, starches, cellulose and cellulose derivatives, gums (e.g., xanthan, locust bean, etc.), and pectin. In one embodiment, the polysaccharides are dextran or mannan.

In one embodiment, the modified polyhydroxylated polymers are prepared by a single one-step reaction. The hydroxyl groups in the polyhydroxylated polymer are modified to feature a functional group selected from the group consisting of acetals, aromatic acetals, ketals, vinyl ethers, aldehydes and ketones. Typically the modification process involves an acid-catalyzed reaction between a polyhydroxylated polymer and functional molecules such as vinyl ethers, acetals, aldehydes, or ketones In one embodiment, the reversible modification of the hydroxyl groups should be carried out to provide modified hydroxyl groups, wherein at least 20%, 25%, 30%, 40%, 50%, 60%, 70%, 75%, 80%, 85%, 90%, 95%, 98%, 99% or 100% of the hydroxyl groups in the polymer are modified. In one embodiment, at least 20-85% of the hydroxyl groups are modified. In another embodiment, at least 75-85% of the hydroxyl groups are modified.

In general, the choice of the polyhydroxylated polymer and the degree of modification also reflects such factors as ease of synthesis, solubility, commercially available reagents, the type of acid-degradable polymer desired, the loading efficiency, dispersion of drug delivery systems comprised of the polymers, toxicity and the hydrolysis rates of the acetal linkage.

In a preferred embodiment, the degradation products are biocompatible and biodegradable. In another embodiment, the degradation products are small molecules as well as polymers with a molecular mass of up to 10,000 daltons or lower, more preferably 1000 daltons, and most preferably 400 daltons or lower. In a preferred embodiment, the degradation product(s) should be non-immunogenic and non-toxic, for example, with the size and/or toxicity levels preferred by one having skill in the art for approved in vivo use.

In another embodiment, the modified polyhydroxylated polymers are modified polysaccharides with pendant acetals, thus providing acetal-derivatized polysaccharides. In one embodiment, the modified polyhydroxylated polymers are acetal-derivatized dextran, acetal-derivatized mannan or acetal-derivatized polyvinyl alcohols.

1. Acid Degradable Linkages

As described above, the modified polyhydroxylated polymers have reversibly modified hydroxyl groups, wherein the hydroxyl groups are modified to feature a functional group selected from the group consisting of acetals, aromatic acetals, ketals. In a preferred embodiment, the functional group is an acetal, aromatic acetal or a ketal. In another embodiment, the modification is made by a one-step reaction.

In a preferred embodiment, the present acid degradable polymers described herein should have a significantly lower rate of degradation in solution at pH 7.4 than at pH 5.

The modified polymers having a modified functional (e.g., acetal or ketal) linkage at the modified hydroxyl groups should degrade by acid catalyzed hydrolysis into lower molecular weight compounds that can be completely excretable. The rate of hydrolysis of these polymers can be changed by varying the functional group (e.g., acetal or ketal) linkage from slow degrading to fast degrading, the degree of modification, or the hydrophobicity of the modification, thus providing a wide range of release kinetics for drug delivery.

Thus, it is contemplated that a variety of acid degradable linkages with different acid-sensitivities can be incorporated onto the polymer backbones using this technology, allowing for excellent control of the rate of polymer hydrolysis.

2. Hydrolysis of the Polymers

Drug delivery systems comprised of the polymers can be hydrolyzed to release their contents in a pH dependent manner. In one embodiment, a feature of the present degradable polymers is the pendant modified hydroxyl groups on the main chain of the modified polyhydroxylated polymer hydrolyzes in a pH dependant manner. In a preferred embodiment the polymers should preferably have a degradation half-life at pH 5.0 of 5 minutes to 24 hours at 37° C., but a longer half life at pH 7.4 of at least 12 hours to 250 days. In the Examples, the degradable polymers have degradation rates at pH 5.0 ranging from half-life of 5 minutes to over 26 hours.

In some embodiments, it may be useful for the polymers to have a half-life at pH 5.0, 37° C. of about 24 hours, and a half-life at pH 7.4, 37° C. of about 250 days, in order to facilitate the slow release of bioactive materials. In other embodiments, it is contemplated that the half-life of polymer degradation at pH 5.0, 37° C. preferably be 5-30 minutes, and even more preferably be less than 5 minutes and a half-life at pH 7.4, 37° C. of about 24 hours in order to quickly release the bioactive materials.

When the modified functional groups are acetals, the acceleration of the hydrolysis kinetics of acetals from pH 7.4 to pH 5.0 is expected because the hydrolysis of the acetal is proportional to the hydronium ion concentration, which should increase between pH 7.4 and pH 5.0. The kinetics of acetal hydrolysis can be easily manipulated by introducing the appropriate electron withdrawing or donating groups and therefore it is possible to engineer degradable polymers that have hydrolysis rates tailor-made for a given application.

A kinetic factor that may be taken into account when designing acid degradable linkages on the modified polyhydroxylated polymer is the acid degradable linkage's speed of hydrolysis in solution. In an embodiment where the goal is to hydrolyze the polymer and rapidly release the bioactive material, the acetal should preferably hydrolyze within 5-30 minutes at pH 5.0 at 37° C. In one embodiment, this timescale is chosen because it is approximately the amount of time taken for a phagocytosed drug delivery system to be trafficked to cellular compartments such as lysosomes. In a preferred embodiment, these particles will degrade rapidly in the lysosome and cause lysosomal destabilization. Having a particle that degrades too slowly will increase its residence time in the lysosome and provide the lysosomal enzymes an increased chance of hydrolyzing the bioactive material before reaching the cytoplasm through lysosomal disruption. Therefore, in a preferred embodiment, the polymer should hydrolyze fairly rapidly at a preferred range of pH 7.4 to 4.5 and even more preferably between pH 6.8 to 4.5.

In one embodiment, the present modified polyhydroxylated polymers are largely stable at pH higher than 7.4 but hydrolyze at a pH preferably about 5. In one embodiment, the modified polymers are soluble in common organic solvents to facilitate processing into a variety of materials. In another embodiment, these modified polymers are not water soluble.

3. Methods for Polymer Modification

Generally, rate of degradation of modified polymers will depend on the degree of modification and the hydrophobicity of the modifying group. For example, in the case of dextran modified with 2-methoxypropene, the degradation rate of the modified polymer will depend on the amount of time that the material is allowed to react.

For acetal modification with vinyl ethers, an example of a method can be as follows. Briefly, the polyhydroxylated polymer is dissolved in an organic solvent such as DMSO and mixed with a vinyl ether and an acid-catalyst such as para-toluene sulfonic acid. Isolation occurs by precipitating the material in water.

For acetal modification with acetals, an example of a method can be as follows. The polyhydroxylated polymer is mixed with an acetal and an acid-catalyst such as para-toluene sulfonic acid over molecular sieves. After reaction, the material is isolated by precipitation into water.

For acetal modification with aldehydes or ketones, an example of a method can be as follows. The polyhydroxylated polymer is mixed with an aldehyde or ketone and an acid-catalyst such as para-toluene sulfonic acid under conditions that remove water (such as azeotropic distillation or molecular sieves). After reaction, the material is isolated by precipitation into water.

4. Bioactive Materials

In a preferred embodiment, the invention contemplates entrapping or conjugation of such bioactive materials including but not limited to, nucleotides, oligonucleotides, polynucleotides, ribonucleotides, amino acids, oligopeptides, polypeptides, peptoids, proteins, antigens, plasmid DNA, growth factors and hormones, interleukins, immunostimulatory agents, drugs, vaccines, neuromodulatory agents such as neurotransmitters, stimulatory and adrenergic agents, enzymes, proteases, anticancer and antitumor agents, imaging agents, diagnostic agents, antiviral agents and antibacterial agents as well as combinations of two or more of these species.

In specific preferred embodiments, the bioactive material is selected from the group consisting of: nucleotides, oligonucleotides, polynucleotides, proteins, oligopeptides, polypeptides, immunostimulatory agents, vaccines, antigens, anti-viral agents, protein antigens, anticancer agents and antitumor agents.

One or more of these bioactive materials can be conjugated to the polymer chains. In one embodiment, the bioactive materials can be conjugated to the polymer through the pendant hydroxyl groups. In another embodiment, materials can be conjugated to the polymer through aldehydes introduced by periodate cleavage of 1,2-diols. In the case where the polyhydroxylated polymers are polysaccharides, latent aldehydes are present at the reducing ends and can be used for modification. The linkage between the polymer chain and the bioactive molecule can be designed to be cleaved under various physiological conditions. The bioactive material can also be adsorbed onto the surface of drug delivery systems, or reacted to the surface of the drug delivery systems. The bioactive material can also be physically trapped inside the drug delivery systems comprised of the modified polyhydroxylated polymers.

5. Drug Delivery Systems

In a preferred embodiment, the modified polyhydroxylated polymers are made into particles for such applications as vaccine delivery. Typical formulations for therapeutic agents incorporated in these delivery systems are well known to those skilled in the art and include but are not limited to solid particle dispersions, encapsulated agent dispersions, and emulsions, suspensions, liposomes or microparticles, wherein said liposome or microparticle comprise a homogeneous or heterogeneous mixture of the therapeutic agent. The amount of the drug that is present in the device, and that is required to achieve a therapeutic effect, depends on many factors, such as the minimum necessary dosage of the particular drug, the condition to be treated, the chosen location of the inserted device, the actual compound administered, the age, weight, and response of the individual patient, the severity of the patient's symptoms, and the like.

In one embodiment, the modified polyhydroxylated polymers made into particles that are 40 to 2000 nm. In general, particles can be synthesized by various techniques, such as double emulsion or spray drying methods, as is known in the art. In one embodiment, the particles can be made according to the procedures described by Liu, R.; Ma, G.; Meng, F.; Su, Z. *J. Controlled Release* 2005, 103, 31-43 and Witschi, C.; Mrsny, J. R. *Pharm. Res.* 1999, 16, 382-390. In a preferred embodiment, the particles are made by double emulsion, single emulsion, or precipitation processes.

Single emulsion and the double emulsion method and precipitation processes can be used to produce particles from sub-micrometer to multi-micrometer sizes; a preferable size range is from 30 nm to 5000 nm, more preferably 30 nm to 2000 nm, and most preferably 40 to 200 nm.

For example, during the double emulsion method, first, the polymer is dissolved in organic solvent along with the surfactants. Then, a small amount of aqueous solution containing the bioactive materials is dispersed into the organic/polymer phase by sonication forming a primary water-in-oil emulsion. This primary emulsion is then dispersed into a larger amount of water containing stabilizers to form a secondary water-in-oil-in-water emulsion. After forming the secondary emulsion, the solution is stirred until the organic phase evaporates. When evaporated, the polymer collapses around the aqueous bioactive material solution forming therapeutic-loaded particles.

In a single emulsion method, the same method is generally used as the double-emulsion method described above, but omitting the first emulsion step with water. There are many nanoprecipitation techniques known to those familiar in the art. One method would be as follows: A solution of 5 mg of Ac-DEX is dissolved in 1 mL of DCM. The DCM is then added dropwise to 10 mL of stirring water and stirred for 6 hours. Particles were isolated by lyophilization in the presence of sucrose as a cryoprotectant. (Biomaterials (2007), 869-87.)

In a preferred embodiment, the acid-degradable polymers are processed to form particles comprised of the modified polyhydroxylated polymers having a bioactive material bound to or entrapped within the formed particles.

In another embodiment, the modified polyhydroxylated polymers are made into drug delivery systems such as a small molecule implant, or time-release device or implant. Methods and compositions useful in making or administering an implant or time-release device in vivo are known and used by one having skill in the art. Examples of such methods and compositions are described in U.S. Pat. Nos. 3,976,071; 5,876,452; 7,077,859; 5,021,241, hereby incorporated by reference. For example, the modified polyhydroxylated polymers of the invention can be prepared in solid form of a needle or bar-like shape or as a bulk shaped material and administered to the body or implanted into the body by injection or an injection-like method and whereby the bioactive material is released at an effective level for a long period of time after administration.

6. Loading and Loading Efficiency of Entrapped Bioactive Materials

Loading efficiency is the amount of bioactive material that is entrapped in or conjugated to within the drug delivery systems comprised of the polymers as compared to the total starting amount of bioactive material placed in the loading reaction.

The loading is the amount of bioactive material contained in the polymer particle, it is generally expressed in mass of bioactive material per unit mass of particle. The loading efficiency and the amount of bioactive material entrapped are important aspects in light of such factors as the amount of bioactive material needed to be delivered to the target for an effective dose and the amount of available bioactive material. A major drawback in previous therapeutics and vaccines is there is often difficulty in obtaining large enough amounts of the therapeutic composition of bioactive material for production. Therefore, it is a goal of the invention to make drug delivery systems with high loading capacities and efficiencies.

In one embodiment, wherein the bioactive material is a small drug molecule for polymer-drug conjugates for applications such as chemotherapy, the degradable polymer particles should exhibit preferred loading as is known in the art. For example, the polymer particles should exhibit high loading efficiency to allow sufficient drug molecules to be conjugated to the polymer or otherwise retained by the polymer without loss of solubility of the overall formulation.

In a preferred embodiment, wherein the bioactive material loaded is DNA material, the loadings and efficiencies of the drug delivery systems should be comparable to other microparticle systems which have efficiencies purported to be about 1-2 µg DNA/mg polymer for 500 nm PLGA particles. (See Garcia del Barrio, G.; Novo, F. J.; Irache, J. M. *Journal of Controlled Release* (2003), 86(1), 123-130). It is estimated that at least about 3,000-7,000 molecules of DNA can be encapsulated within a single degradable polymer particle of the present invention, if the DNA encapsulated was 6,000 bp, which has a MW of about 4 million daltons. The loading efficiencies for the amount of DNA material entrapped in degradable particles of the preferred embodiment should preferably be at least 40%, more preferably at least 50% and even more preferably at least 54%. Loadings for bacterial DNA for immunostimulation purposes should be around 1-30 µg DNA/mg.

In a preferred embodiment, wherein the bioactive material loaded is protein, the loading efficiencies for the amount of protein entrapped in particles comprised of the acid degradable polymers of the preferred embodiment should be at least 20%, preferably at least 40%, more preferably around 50%, and most preferably >90%.

7. Toxicity of Polymers and Polymer Degradation Products

Use of this invention in human and mammalian therapeutics brings up issues of the toxicity of these polymers. The viability of cells can be measured by the ability of mitochondria in metabolically active cells to reduce yellow tetrazolium salt (MTT) in the classical MTT assay to form formazan crystals.

In a preferred embodiment, the target cells should preferably exhibit at least 50% viability after 24 hours of incubation with the polymers of the invention, more preferably at least 70% viability after 24 hours, even more preferably at least 80% viability and most preferably more than 90% viability after 24 hours according to the MTT assay.

Polymers with high MW are not easily excreted from the body, therefore another aspect of the invention is to make polymers that are easily and safely excreted by the body after being degraded in the acidic environments. In general it is preferred that the polymers degrade into many small molecules and/or molecules that are non toxic and readily excreted from the body. The degradation products of the present modified polyhydroxylated polymers of the invention should be easily excreted from body due to the small molecule size of the degradation products produced after hydrolysis of the pendant modified groups and the use of a main chain polyhydroxylated polymer that is biocompatible (e.g., a polysaccharide such as dextran). Another aspect of the invention is to make particles that are easily and safely excreted by the body after being degraded in the acidic cellular compartment. In general it is preferred that the particles degrade into degradation products that are linear polymers and/or smaller molecules (e.g., 10,000 daltons or less), and that the degradation products are not toxic to a mammalian subject.

B. Applications for Modified Polyhydroxylated Polymers

This strategy for the synthesis of modified polyhydroxylated polymers has many applications including the delivery of bioactive materials, including but not limited to polynucleotides, polypeptides, proteins, peptides, organic molecules, antibodies, vaccines, antigens, genetic agents, small drugs or therapeutic agents, into the cytoplasm of phagocytic cells, site of inflammation, tumor tissues, endosomes, or other sites of low pH. These materials can also be fashioned into bulk materials such as sutures, scaffolds, and implants.

1. Vaccine Therapeutics

In one embodiment, the polymers of the present invention would have applications in vaccine therapeutics and disease prevention. Protein loaded particles prepared using these polymers could be injected into a patient, stimulating phagocytosis by macrophages and antigen presenting cells.

In one embodiment, the acid-degradable modified polyhydroxylated polymer particles are delivered to antigen presenting cells and then phagocytosed and trafficked to the lysosome or phagolysosome of the cells. The mild acidic conditions found in lysosomes and phagolysosomes of APCs should cause the pendant acetal groups along the polymer backbones to be hydrolysed thereby degrading the particles. This acid hydrolysis of the acid-degradable linkage causes degradation of the polymers.

The particles comprised of the acid degradable polymers of the invention would be particularly useful in combating infections that need a strong cytotoxic T lymphocyte response, including diseases such as HIV/AIDS and Hepatitis C infections. Examples of such antigens which can be used as bioactive material and entrapped in the particles of the present invention, include but are definitely not limited to, the TAT protein from HIV, the ENV protein from HIV, the Hepatitis C Core Protein from the Hepatitis C virus, the prostatic acid phosphatase for prostate cancer and the protein MART-1 for melanoma.

In one embodiment, the modified polyhydroxylated polymers particles enhance CTL activation by dendritic cell (DC)-targeting. OVA is encapsulated in acid-degradable polymeric particles further conjugated with anti-DEC-205 mAbs monoclonal antibody. The particles are taken up by DEC-205 expressing dendritic cells in vivo. After hydrolysis in the acidic lysosome of DCs, encapsulated OVA is released into the cytoplasm.

In another embodiment, signal peptides are attached to the particle. Any suitable signal peptide can be used in the particles of the invention. The peptide should be able to target (i.e., mediate entry and accumulation) a particle to a subcellular compartment and/or organelle of interest. Signal peptides are typically about about 5 to about 200 amino acids in length. Suitable signal peptides include, e.g., nuclear localization signal peptides, peroxisome-targeting signal peptides, cell membrane-targeting signal peptides, mitochondrial-targeting signal peptides, and endoplasmic reticulum-targeting signal peptides, and trans-Golgi body-targeting signal peptides. Signal peptides may also target the particles to any cell surface receptor including e.g. epidermal growth factor receptors (EGFR), fibroblast growth factor receptors (FGFR), vascular endothelial cell growth factor receptor (VEGFR), integrins, chemokine receptors, platelet-derived growth factor receptor (PDGFR), tumor growth factor receptora, and tumor necrosis factor receptors (TNF).

Nuclear localization signal peptides typically comprise positively charged amino acids. Endoplasmic reticulum targeting signal peptides typically comprise about 5 to about 10 hydrophobic amino acids. Mitochondria targeting signal peptides are typically about 5 to about 10 amino acids in length and comprise a combination of hydrophobic amino acids and postively charged amino acids. Peroxisome targeting signal peptides include PTS1, a 3 amino acid peptide and PTS2, a 26-36 amino acid peptide. Examples of signal peptide sequences include but are not limited to the following sequences in Table 1.

TABLE 1

| Target | Source | Sequence |
|---|---|---|
| Nucleus | SV-40 large T antigen | PPKKKRKVPPKKKRKV (SEQ ID NO: 1) |
| Nucleus | Tat protein of HIV | YGRKKRRQRRR (SEQ ID NO: 2) |
| Endoplasmic Reticulum | | KDELA KDELA KDELA KDEL (SEQ ID NO: 3) |
| Mitochondria | Cytochrome C oxidase | SVTTPLLLRGLTGSARRLPVPRAKIHSL (SEQ ID NO: 4) |
| Peroxisome | | SKLA SKLA SKLA SKLA (SEQ ID NO: 5) |
| Cell Membrane | | KLNPPDESGPCMSCKCVLS (SEQ ID NO: 6) |
| Cell Membrane | GAP-43 | MLCCMRRTKQVEKNDEDQKI (SEQ ID NO: 7) |

Signal peptides can be chemically synthesized or recombinantly produced. In general, the nucleic acid sequences encoding signal peptides and related nucleic acid sequence homologues are cloned from cDNA and genomic DNA libraries or isolated using amplification techniques with oligonucleotide primers. Standard techniques are used for nucleic acid and peptide synthesis, cloning, DNA and RNA isolation, amplification and purification. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

In another embodiment, the particles are decorated with a targeting functional group or other cell penetrating peptides to penetrate non-phagocytic cells. For example, targeting functional groups include antibodies, various oligopeptides, or carbohydrate moieties, Cell-penetrating peptides can also include oligopeptides such as oligomers of arginine or polymers rich in arginine motifs.

In one embodiment, immunostimulatory groups are attached to, displayed on, or encapsulated in the particle. Examples of immunostimulatory groups include but are not limited to mannose, plasmid DNA, oligonucleotides, ligands for the Toll-like receptors, interleukins and chemokines. T-cells activate B-cells to secrete Interleukin-6 (IL-6) to stimulate B cells into antibody-secreting cells.

In another embodiment, targeting antibodies are attached to the particle. Any antibody specific for a target in vivo can be attached to the particle to target and allow particle delivery of the bioactive material.

For example, in one embodiment, the acid-degradable polymers particles enhance CTL activation by dendritic cell (DC)-targeting as described above.

2. Gene Therapy

In another embodiment, the polymers of the invention would be used to prepare drug delivery systems for gene therapeutics. Cationic polymers would be especially relevant for this application because polycations can complex with DNA. Since gene therapy involves the delivery of a sequence of DNA to the nucleus of a cell, the particles comprised of these polymers of the invention would be especially suited for this application. Once a polynucleotide is delivered by the drug delivery systems to the cytoplasm, the polynucleotide can undergo translation into a protein. This has the potential, then, to make proteins that are not normally produced by a cell.

In a preferred embodiment, the bioactive material is a plasmid that encodes for a protein or antigenic peptide initially. For example, one would use a plasmid that encodes for a protein that would display antigens for cancer. These proteins are not easy to generate in multi-milligram to gram quantities to be delivered to a patient, therefore using the present particle delivery systems prepared with polymers of the present invention to deliver plasmid DNA encoding these antigens is a preferred alternative.

In addition to encoding for a gene, plasmid DNA has the added characteristic of generating an immune response because plasmid DNA is generated from bacteria. Other potential bioactive materials are CpG oligonucleotides that are also derived from bacterial DNA. Bacterial DNA has two major differences compared with vertebrate DNA: 1) bacterial DNA has a higher frequency of CG dinucleotides in the sequence ($1/16$ dinucleotides in microbial DNA are CG pairs, but only 25% of that is observed in vertebrate DNA); and 2) bacterial DNA is unmethylated as compared to vertebrate DNA which is often methylated. Vertebrate systems will recognize the DNA then as being foreign, and the cell should react as for a bacterial infection. This immune response is manifested in the production of cytokines and interleukins that then go on to activate T cells, B cells, and other cells, proteins, and cellular machinery involved in the immune response.

3. Directing Patient Immune Response Using the Helper T-Cell Response

In a further embodiment, the plasmid DNA used as the bioactive material would have an added interleukin sequence. (Egan, Michael A.; Israel, Zimra R. *Clinical and Applied Immunology Reviews* (2002), 2(4-5), 255-287.) Interleukins are secreted peptides or proteins that mediate local interactions between white blood cells during immune response (B. Alberts et al, *Molecular Biology of the Cell*, 4th ed., Garland Science, 2002). Different interleukins (e.g. IL-12, IL-2) will direct the type of immune response that is generated. IL-6, IL-1, IL-8, IL-12, and TNF-α are secreted by infected macrophages as an immune response and IL-6 serves to activate lymphocytes and increase antibody production. The differentiation of helper T cells into either $T_H1$ or $T_H2$ efffector cells determines the nature of the response. A $T_H1$ response is characterized by a CTL response; a $T_H2$ response is characterized by antibody production.

It has been shown by Apostolopoulos, V.; McKenzie, I. F. C. *Current Molecular Medicine* (2001), 1(4), 469-474, that activation of the mannose receptors on the surface of APCs leads to enhanced CTL activation. Thus, the addition of the interleukin-2 or 12 (IL-2 or IL-12) gene sequence, and its subsequent translation into an interleukin protein may allow the direction of the type of patient immune response and amplification of the desired CTL response by adding or displaying immunostimulatory groups on the surface of the particles. Such immunostimulatory groups include but are not limited mannose, plasmid DNA, oligonucleotides, ligands for the Toll receptors, interleukins and chemokines. T-cells activate B-cells to secrete Interleukin-6 (IL-6) to stimulate B cells into antibody-secreting cells.

4. Drug Delivery Systems and Dispersion

In a preferred embodiment, bioactive drug molecules may be temporarily attenuated by incorporation into modified polyhydroxylated polymers for applications such as chemotherapy. Drug molecules may be incorporated into the polymers covalently, where the drug molecules are attached to the main polyhydroxylated polymer chain via labile linkages. Water soluble polymer-drug conjugates will preferably be administered intravenously or orally, and biologically active drug molecules will be released from the polymer upon cleavage of the labile polymer-drug linkages. Drug molecules may also be incorporated noncovalently by entrapment of drugs into particles or implant devices fashioned from water insoluble variants of the acid-degradable polymers. Water insoluble polymers will preferably be administered orally or will be implanted in the body, and drug molecules will be released from the polymer upon degradation of the polymer matrix in which the drug is entrapped or conjugated.

Drug delivery systems comprised of the invention may be suspended or stored in a conventional nontoxic vehicle, which may be solid or liquid, water, saline, or other means which is suitable for maintaining pH, encapsulation of the bioactive material for an extended period of time, sufficient dispersion or dilution of the delivery systems and the overall viability of the delivery systems for their intended use.

Preferably the delivery systems comprised of the polymers of the invention are stored in dry state (vacuum dried) and stored at 4° C. for several months. The systems may be dispersed in buffer and sonicated or vortexed for a few minutes to resuspend into solution when needed.

5. Delivery of RNAi Agents.

In a preferred embodiment, the polymers of the invention can be used to prepare delivery systems for RNA interference (RNAi) agents such as small interfering RNA (siRNA), long double-stranded RNA (dsRNA) or short hairpin RNA (shRNA). In one embodiment siRNA in the form of double stranded RNA molecules less than 40 nucleotides in length can be encapsulated in polymers of the invention. Encapsulation efficiency can be improved using cationic lipids such as DOTAP (N-[1-(2,3-Dioleoyloxy)propyl]-N,N,N-trimethylammonium methylsulfate) or cationic polymers such as PEI (polyethyleneimine) or poly-β-aminoesters. Materials delivering siRNA have the potential to interfere with cellular protein production. This may be therapeutically relevant for treating many different genetic or pathogenic diseases as well as cancer.

6. Pharmaceutically Effective Delivery and Dosages

The loaded drug delivery systems of the invention can be administered by various suitable means to a patient, including but not limited to parenterally, by intramuscular, intravenous, intraperitoneal, or subcutaneous injection, or by inhalation. The delivery of the systems to a patient is preferably administered by injection once but does not preclude the necessity for multiple injections that would be required to illicit the desired response. In another embodiment, the delivery system is an implant system, wherein the polymer is implanted into an affected tissue, such as a tumor, and allowed to degrade and release the bioactive material. For example, water insoluble degradable polymers are implanted in the body, and drug molecules will be released from the polymer upon degradation of the polymer matrix in which the drug is entrapped.

The amount of delivery vehicle needed to deliver a pharmaceutically effective dosage of the bioactive material will vary based on such factors including but not limited to, the polymer solubility, the therapeutic loading capacity and efficiency, the toxicity levels of the polymers, the amount and type of bioactive material needed to effect the desired response, the subject's species, age, weight, and condition, the disease and its severity, the mode of administration, and the like.

One skilled in the art would be able to determine the pharmaceutically effective dosage. In general, the amount of bioactive material that could be administered by the delivery systems of the invention is from 1 ng to more than 1 g quantities.

Example 1

Synthesis and Characterization of Acid-Degradable Acetal-Derivatized Dextran

We sought to create a system with the flexibility and biocompatibility of polyester materials, but with the additional benefit of a change in rate of payload release that is sensitive to physiologically relevant acidic conditions. We discovered a solubility switching mechanism in which a biocompatible, water-soluble polymer could be reversibly modified to make it insoluble in water, but soluble in organic solvents. Materials made from the modified polymer could then be degraded under the specific conditions that reverse the original modification. Dextran, a bacterially derived homopolysaccharide of glucose, was chosen to be modified because of its biocompatibility, biodegradability, wide availability, and ease of modification ((a) Hermanson, G. T., *Bioconjugate Techniques*. Academic Press: San Diego, 1996 (b) Naessens, M.; Cerdobbel, A.; Soetaert, W.; Vandamme, E. J., *J. Chem. Technol. Biotechnol.* 2005, 80, 845-860). Acetals were chosen to modify dextran due to their well understood and tunable pH-dependant hydrolysis rates (Fife, T. H.; Jao, L. K., *J. Org. Chem.* 1965, 30, 1492-&).

Figure 4:
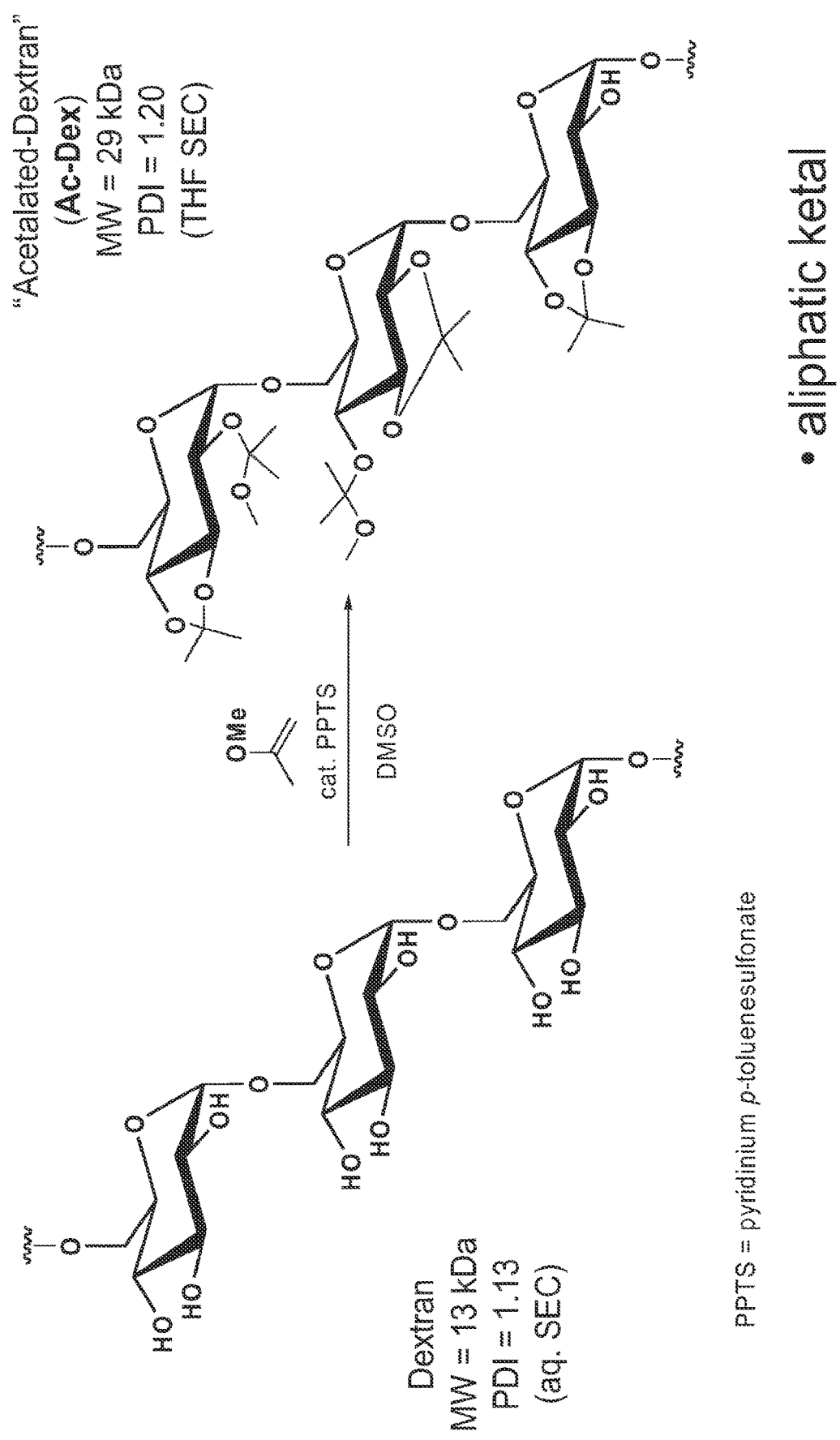
FIG. 4 shows the scheme for synthesis of dextran modified to dextran having cyclic and acyclic ketals masking the hydroxyl groups.
Figure 5:
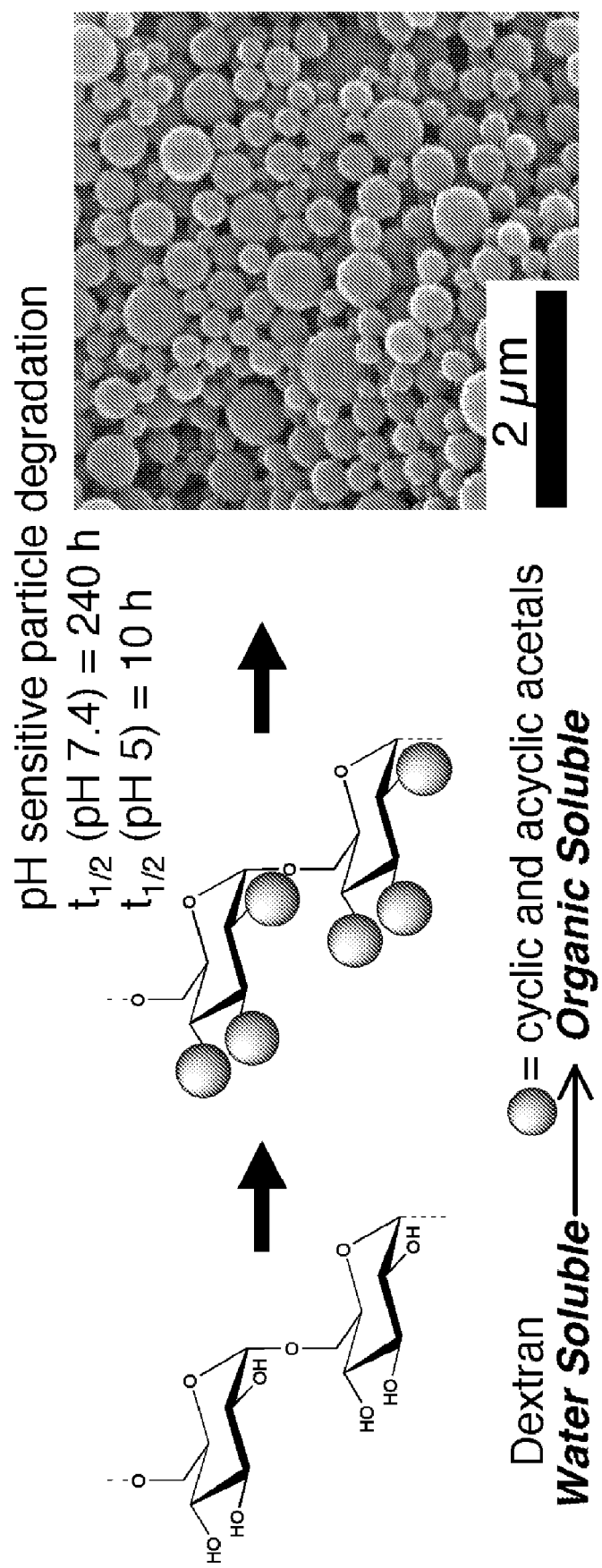
FIG. 5 shows water-soluble dextran modified to organic-soluble dextran having cyclic and acyclic acetals masking the hydroxyl groups and anSEM image of the Ac-DEX particles.
Figure 6:
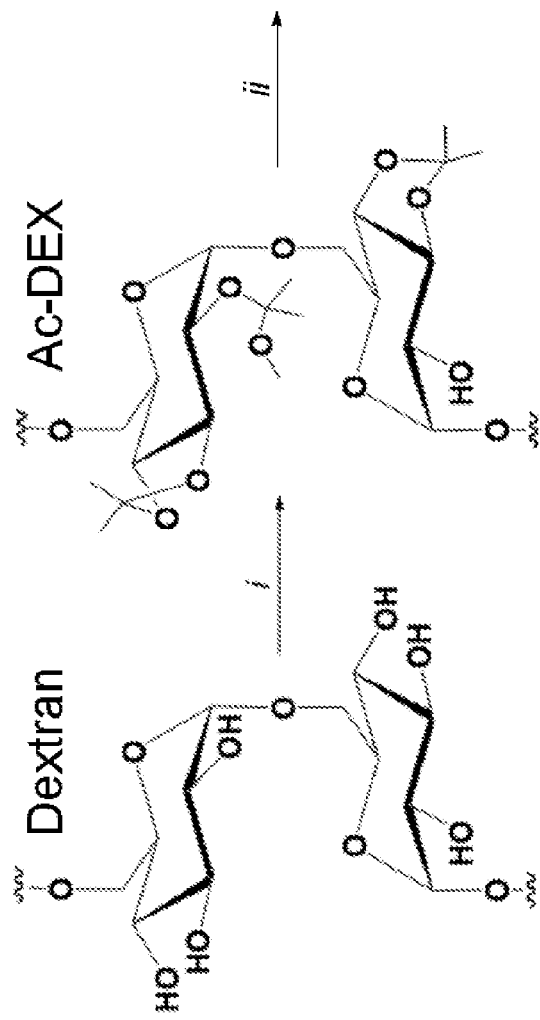
FIG. 6 shows the synthesis of acetal-modified dextran (Ac-DEX) and particle formation (i) 2-methoxypropene, pyridinium-p-toluenesulfonate, DMSO (ii) solvent-evaporation-based particle formation (scale bar is 2 μm).
Figure 7:
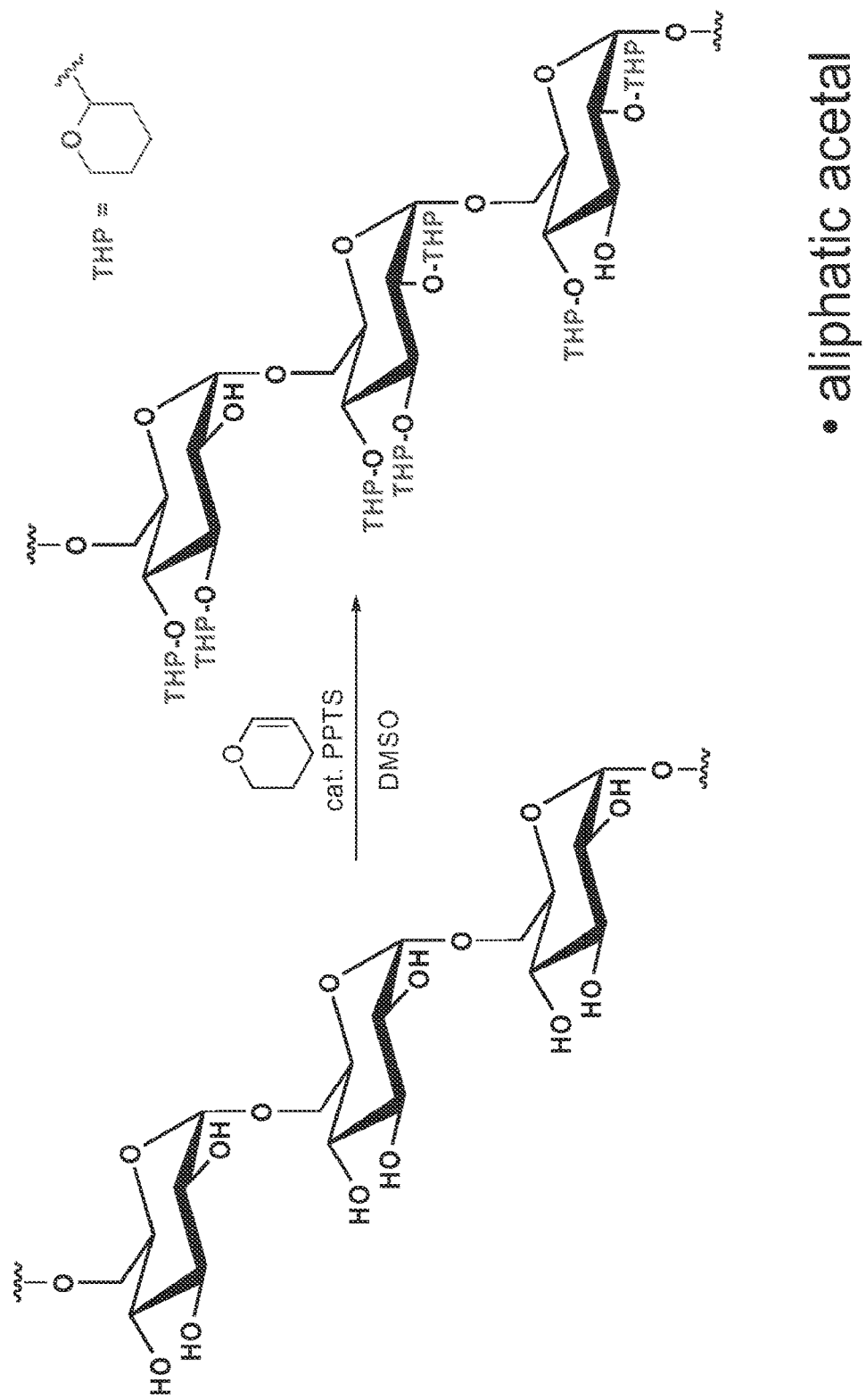
FIG. 7 shows the scheme for synthesis of dextran modified to dextran having aliphatic acetals masking the hydroxyl groups.
Figure 8:
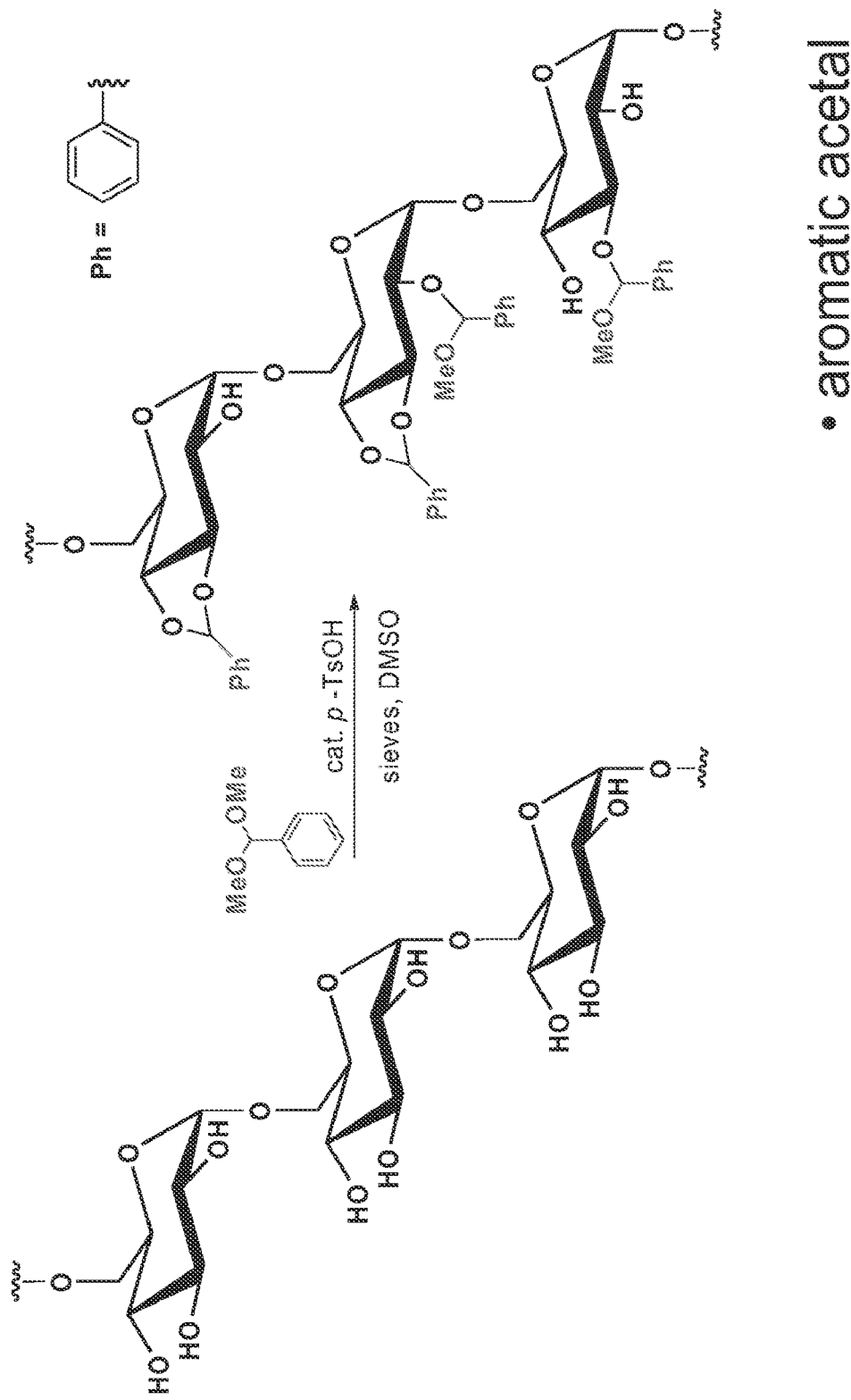
FIG. 8 shows the scheme for synthesis of dextran modified to dextran having aromatic acetals masking the hydroxyl groups.
Figure 9:
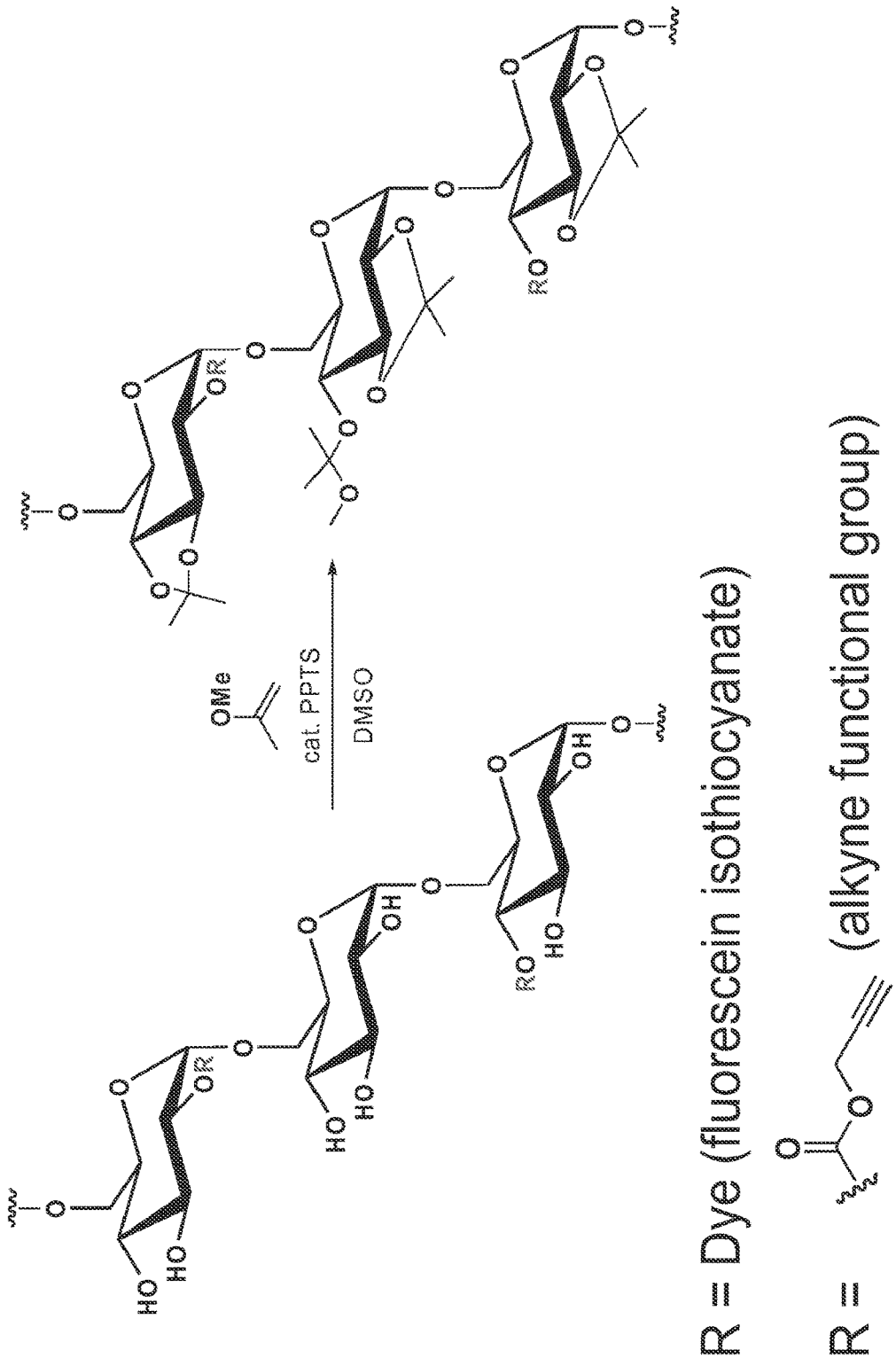
FIG. 9 shows the scheme for synthesis of pre-functionalized dextran having alkyne functional groups or a dye to prefunctionalized dextran having cyclic and acyclic ketals masking the hydroxyl groups.
Figure 12:
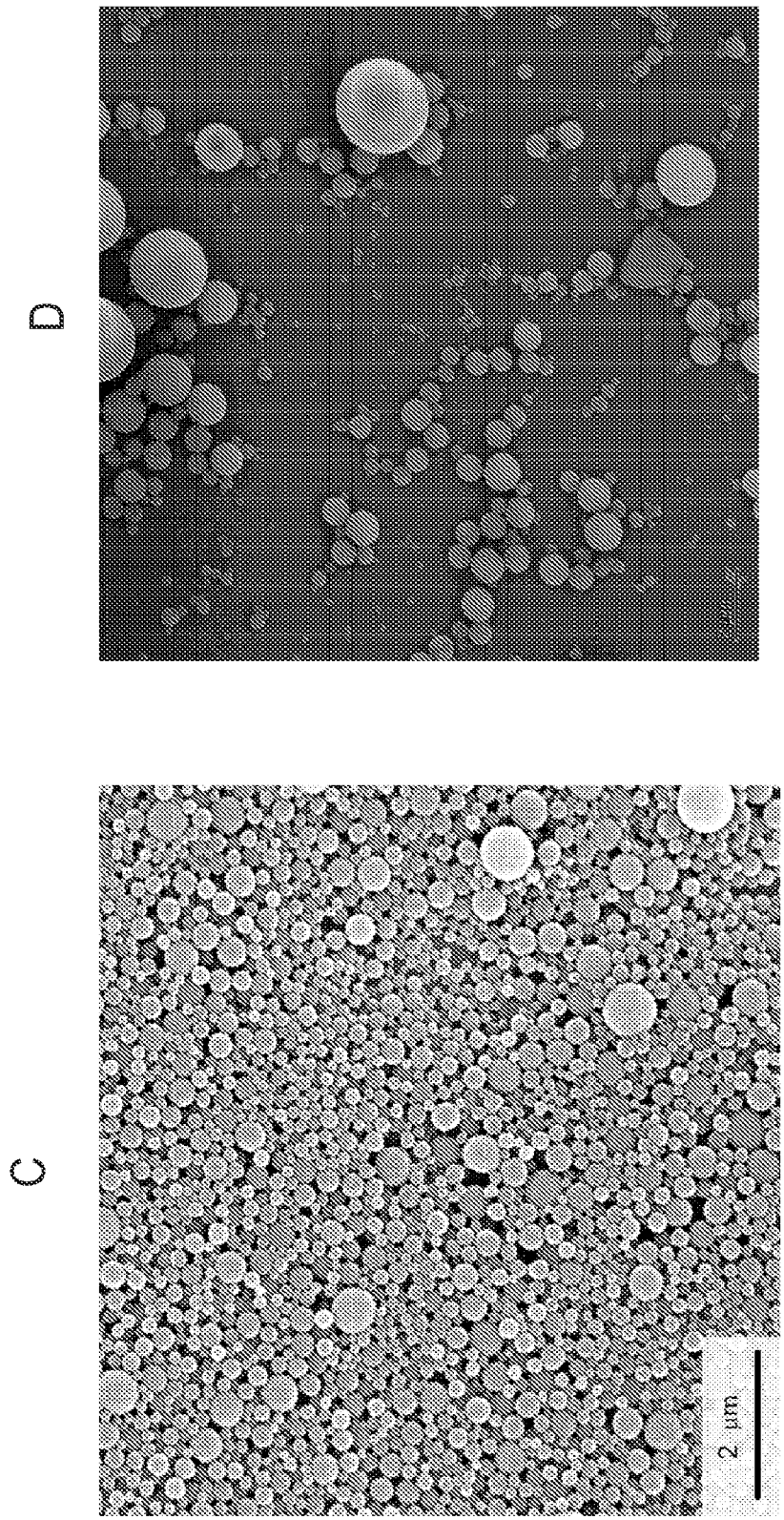
FIG. 12. Representative SEM image of (A) Ac-DEX particles, (C)single emulsion Ac-DEX particles and (D) single emulsion acetalated mannan particles.
Figure 16:
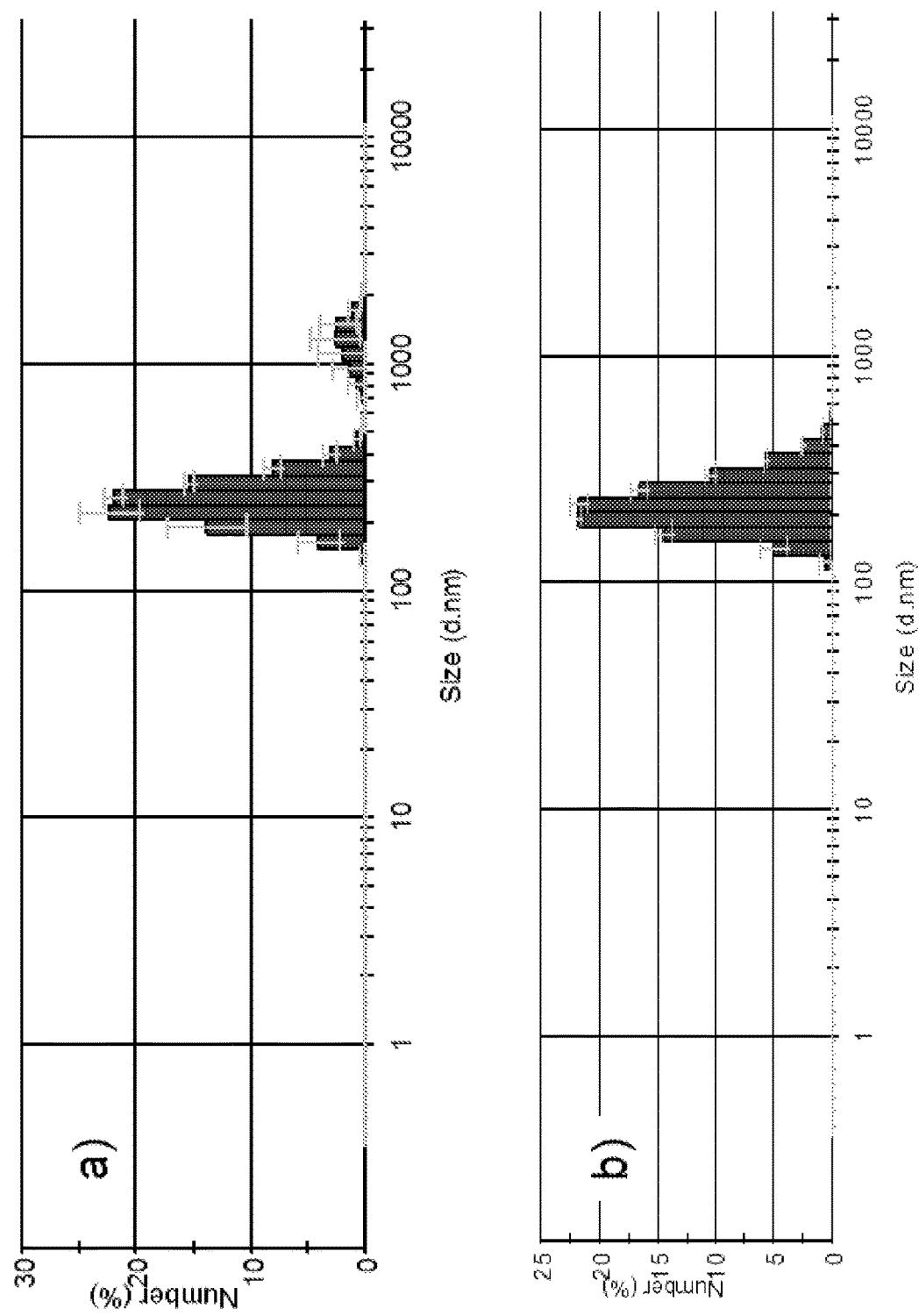
FIG. 16. Size distribution histograms of (a) double emulsion particles encapsulating OVA or (b) single emulsion particles encapsulating pyrene. The results in the text are presented as average particle diameters±half width of the distribution at half maximal height FIG. 17. Release profile of FITC-dextran encapsulated in Ac-DEX particles at 37° C. and in pH 5 or pH 7.4 buffer.

Dextran was rendered insoluble in water by modification of its hydroxyl groups through reaction with 2-methoxypropene under acid catalysis (FIG. 4, 6). The high density of pendant acetals makes the new "acetalated-dextran" (Ac-DEX) soluble in organic solvents such as dichloromethane, ethyl acetate or acetone. Based on multi-angle light scattering data, the molecular weight of the dextran increases upon modification from 13 kDa to 29 kDa while the polydispersity remains essentially constant (1.13 to 1.20), suggesting coverage of the hydroxyl groups and minimal polymer cross-linking. Using a standard double emulsion protocol, a model hydrophilic payload, ovalbumin (OVA), was encapsulated with a protein loading of 3.7±0.4 wt % (FIG. 6). Using a single emulsion technique, we were able to encapsulate a model hydrophobic drug, pyrene, with a loading of 3.6±0.5 wt %. The particles were imaged using scanning electron microscopy (FIG. 12A) and particle size was analyzed using dynamic light scattering. The double emulsion particles were found to have an average diameter of 230±13 nm (FIG. 16) and the single emulsion particles had similar shapes and sizes with an average diameter of 258±1 nm.

Figure 14:
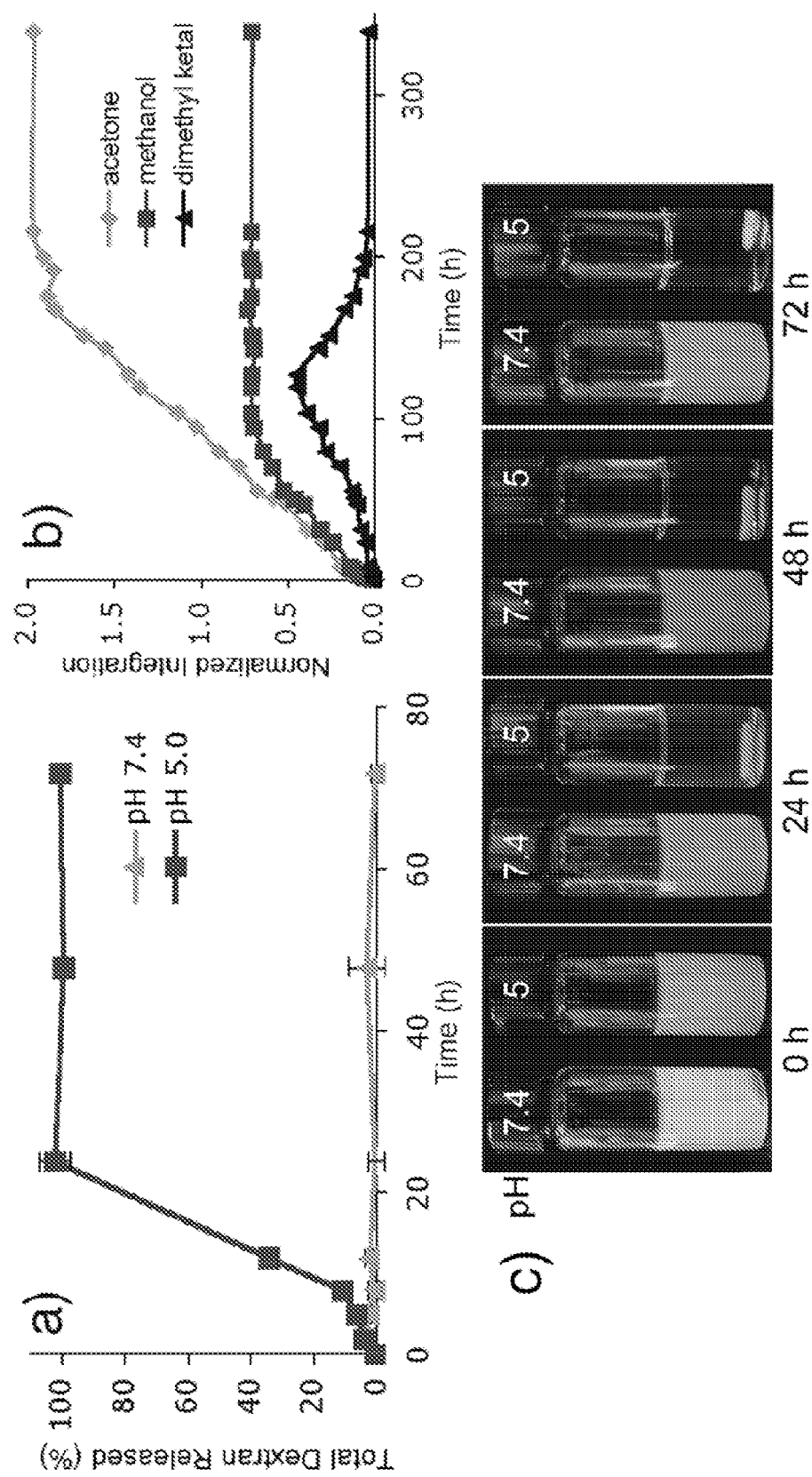
FIG. 14 (a) Dissolution of dextran from Ac-DEX particles in either pH 5 or pH 7.4 buffer at 37° C. (b) Normalized $^1$H-NMR data from the degradation of Ac-DEX particles at pH 5.5 and 37° C. showing integrations of signals corresponding to acetone, methanol and acetal groups. (c) Time-lapse photos of Ac-DEX particles under physiological or acidic conditions.
Figure 17:
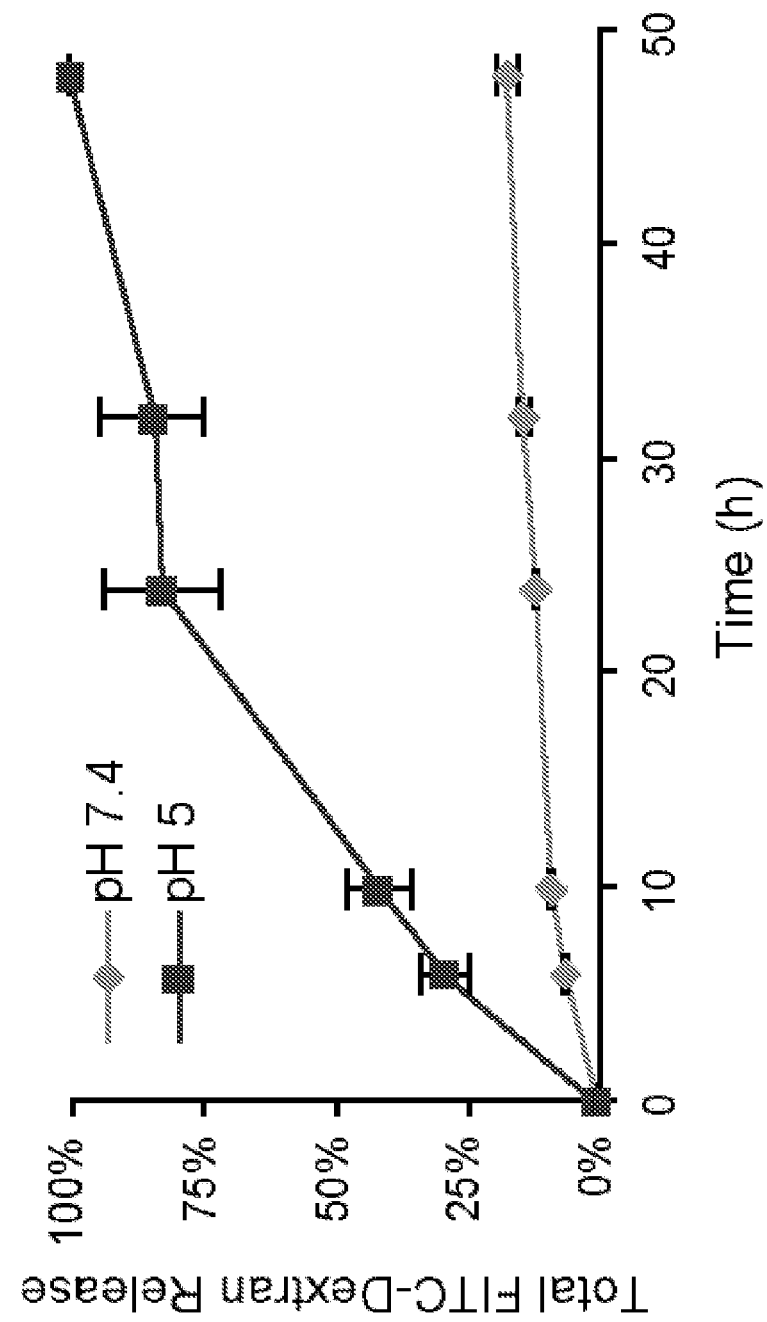

Masking the hydroxyl groups of dextran as acetals not only provides a hydrophobic material that is easily processable using various emulsion techniques, it also provides a mechanism for introducing pH-sensitivity. Under mildly acidic aqueous conditions, the pendant acetal groups are expected to hydrolyze, thus unmasking the parent hydroxyl groups of dextran. The complete hydrolysis of Ac-DEX should result in the release of acetone, methanol and water-soluble dextran. To study the degradation of Ac-DEX, empty particles were prepared and incubated under physiological (pH 7.4) or mildly acidic conditions (pH 5.0) at 37° C. The supernatant was analyzed at various times for the presence of reducing polysaccharides using a bicinchoninic acid based assay (Doner, L. W.; Irwin, P. L., *Anal. Biochem.* 1992, 202, 50-53). Ac-DEX particles incubated in pH 7.4 buffer remained as an opaque suspension for days and essentially no soluble dextran was detected after 72 hours (FIG. 14a,c). In contrast, suspensions of Ac-DEX particles in pH 5.0 buffer showed continuous release of soluble reducing polysaccharides, becoming transparent after 24 hours, thus suggesting full dissolution of the particles. This pH-dependent degradation of Ac-DEX particles is further reflected in the release profile of a model fluorescently labeled hydrophilic payload (FIG. 17). In this experiment fluorescein isothiocyanate (FITC) labeled dextran was released from Ac-DEX particles much faster under acidic conditions than in pH 7.4 buffer. Specifically, the half-life of the release of FITC-dextran at 37° C. and pH 5.0 was about 10 hours compared to approximately 15 days at pH 7.4.

Figure 18:
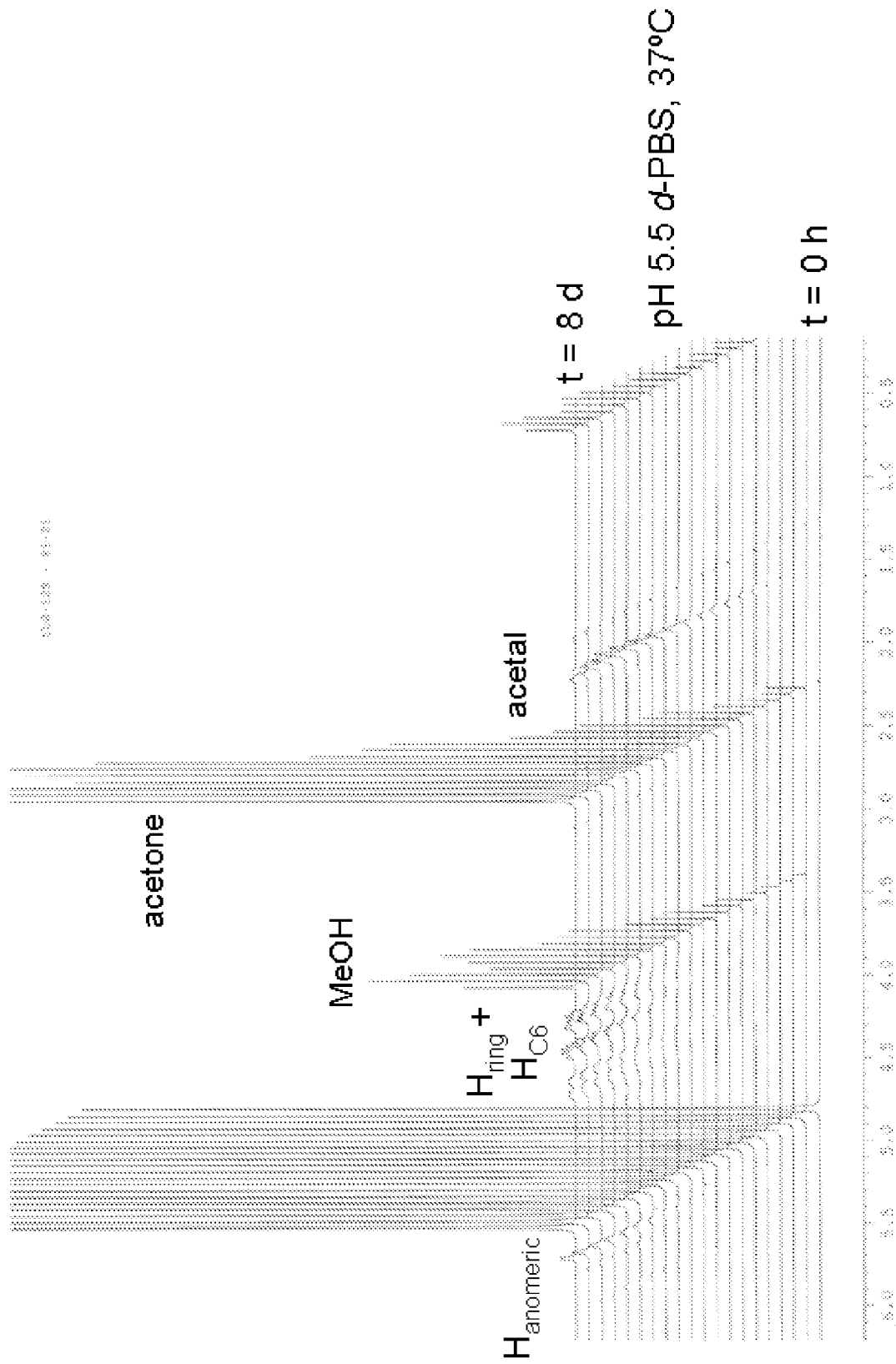
FIG. 18. Stack plot of $^1$H NMR spectra of empty Ac-DEX particles incubated in deuterated pH 5.5 buffer over time. Spectra are shown for the first eight days and are normalized with respect to the integration of the TMS peak.
Figure 19:
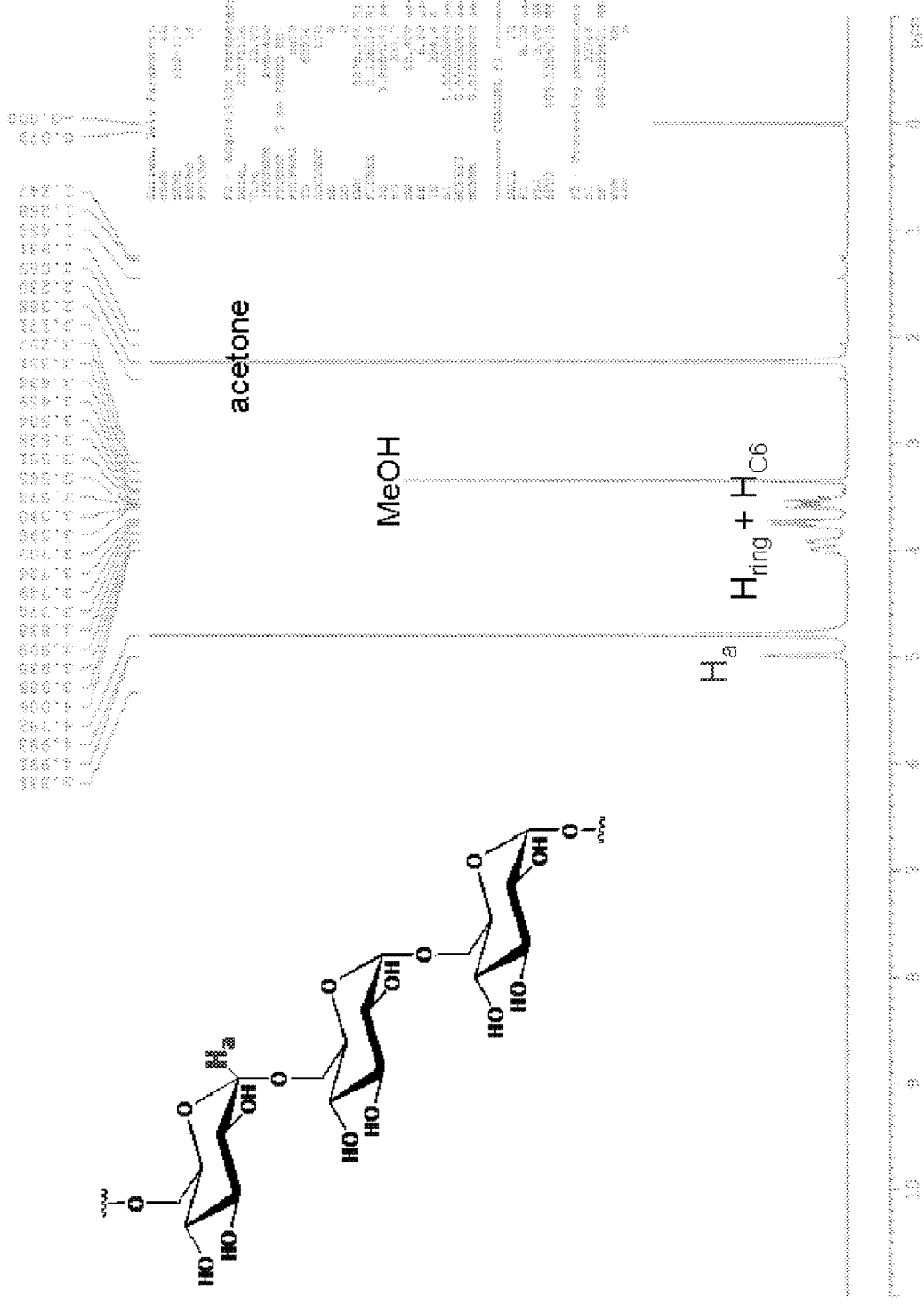
FIG. 19. Final $^1$H NMR spectrum of degraded Ac-DEX particles.

The degradation of empty Ac-DEX particles was also followed using $^1$H-NMR. A suspension of particles was incubated at 37° C. in deuterated PBS (pH 5.5) in a flame-sealed NMR tube. The release of acetone and methanol due to acetal hydrolysis was observed and the normalized integrals of these compounds were plotted as a function of time (FIG. 14c and FIG. 18). The particles first released a roughly equivalent amount of acetone and methanol, which is consistent with the rapid hydrolysis rate of pendant acyclic acetals. (Fife, T. H.; Jao, L. K., *J. Org. Chem.* 1965, 30, 1492-&) Following this phase, acetone, but not methanol continued to be released from the degrading particles. This second phase is presumably due to the slower hydrolysis rate of cyclic isopropylidene acetals, signals from which appear, then subsequently disappear as the acetals are hydrolyzed ((a) Cai, J. Q.; Davison, B. E.; Ganellin, C. R.; Thaisrivongs, S., *Tetrahedron Lett.* 1995, 36, 6535-6536 (b) Debost, J. L.; Gelas, J.; Horton, D.; Mols, O., *Carbohydr. Res.* 1984, 125, 329-335). Following complete hydrolysis, the $^1$H-NMR spectrum of the degraded particles showed signals corresponding only to unmodified dextran, acetone and methanol (FIG. 19). Based on this final spectrum, it was calculated that 73% of the available hydroxyl groups were modified and the ratio of cyclic to acyclic acetals was estimated at 1.8:1. These values were calculated using the integration of the acetone and methanol signals compared to the integration of the anomeric proton.

We have previously shown that acid-labile polyacrylamide particles enhance protein-based vaccine efficacy in cancer treatment by enhancing MHC class I presentation and CD8$^+$ T cell activation ((a) Murthy, N.; Xu, M.; Schuck, S.; Kunisawa, J.; Shastri, N.; Frechet, J. M., *Proc. Natl. Acad. Sci. U.S.A* 2003, 100, 4995-5000 (b) Standley, S. M.; Kwon, Y. J.; Murthy, N.; Kunisawa, J.; Shastri, N.; Guillaudeu, S. J.; Lau, L.; Frechet, J. M. *J., Bioconjugate Chem.* 2004, 15, 1281-1288). However, because the particles are prepared from acrylamide, toxicity and biocompatibility issues might limit future clinical applications. Ac-DEX based particles are expected to be more "bio-friendly" than our previous system since the byproducts are dextran (a clinically used plasma expander), acetone (a non-toxic, metabolic intermediate) and methanol (non-toxic in small quantities). Paine, A; Davan, A. D.; *Hum. Exp. Toxico.* 2001, 20, 563-568.

Thus, we present a new method for the preparation of acid-sensitive, biocompatible dextran-based materials. Ac-DEX is easily synthesized and processed into materials encapsulating either hydrophobic or hydrophilic payloads. Particles made from Ac-DEX become soluble in slightly acidic environments, releasing their cargo. Finally, due to their favorable toxicity profiles, these particles should find use in drug delivery applications demanding pH-sensitive and biocompatible materials. We are currently investigating the functionalization and use of these and other modified polysaccharides in vaccine and chemotherapeutic settings. In addition, we believe Ac-DEX has the potential to be used as scaffolds, sutures, and other bulk materials in vivo due to its physical properties, biodegradability, and biocompatibility.

Example 2

Materials and Methods for the Examples
General Procedures and Materials.

All reagents were purchased from commercial sources and used without further purification unless otherwise specified. Water (dd-H$_2$O) for buffers and particle washing steps was purified to a resistance of 18 MS) using a NANOpure purification system (Barnstead, USA). When used in the presence of acetal containing materials, dd-H$_2$O was rendered basic (pH 8) by the addition of triethylamine (TEA) (approximately 0.01%). $^1$H NMR spectra were recorded at 400 MHz and $^{13}$C spectra were recorded at 100 MHz. To prevent acid catalyzed hydrolysis of acetal containing compounds, CDCl$_3$ was passed through a plug of basic alumina prior to recording NMR spectra. Multiangle light scattering (MALS) experiments were performed with a Waters 510 pump, a 7125 Rheodyne injector, a Wyatt Optilab differential refractive index detector and a Wyatt DAWN-EOS MALS detector. Absolute molecular weights determined from light scattering data were calculated using Astra software from Wyatt assuming a quantitative mass recovery (online method). Columns were thermostatted at 35° C. MALS experiments run with THF as a solvent were performed using two 7.5×300 mm PLgel mixed-bed C columns with a 5 micron particle size. MALS experiments run in aqueous conditions were performed using dd-H$_2$O with 5% acetic acid as a solvent and Viscotek C-MBMMW-3078 and C-MBHMW-3078 cationic columns (7.8 mm×300 mm) in series. Fluorescence measurements were obtained on a Fluorolog FL3-22 spectrofluorometer (Horiba Jobin Yvon) or a Spectra Max Gemini XS (Molecular Devices, USA) for microplate-based assays. Fourier transform infrared spectroscopy (FT-IR) was carried out on a 3100 FT-IR spectrometer (Varian, USA). UV-Vis spectroscopic measurements were obtained from samples in quartz cuvettes using a Lambda 35 spectrophotometer (Perkin Elmer, USA) or using a Spectra Max 190 (Molecular Devices, USA) for microplate-based assays. RAW 309 and HeLa cells were obtained from ATCC (Manassas, Va.) and grown according to ATCC's directions.

Example 3

The Acetalation of Water-Soluble Polyhydroxylated Polymers Resulting in pH-Sensitive Hydrophobic Polymers: Examples of Modification of Polyhydroxylated Polymers Synthesis of Acetalated Dextran (Dimethyl Acetal Dextran: Ac-DEX).

A flame-dried flask was charged with dextran ($M_w$=10 500 g/mol, 1.00 g, 0.095 mmol) and purged with dry $N_2$. Anhydrous DMSO (10 mL) was added and the resulting mixture was stirred until complete dissolution of the dextran was observed. Pyridinium p-toluenesulfonate (15.6 mg, 0.062 mmol) was added followed by 2-methoxypropene (3.4 mL, 37 mmol). The flask was placed under a positive pressure of $N_2$, then sealed to prevent evaporation of 2-methoxypropene. After 6 h, the reaction was quenched with TEA (1 mL, 7 mmol) and the modified dextran was precipitated in dd-$H_2O$ (100 mL). The product was isolated by centrifugation at 4 600×g for 10 min and the resulting pellet was washed thoroughly with dd-$H_2O$ (2×50 mL, pH 8) by vortexing and sonication followed by centrifugation and removal of the supernatant. Residual water was removed by lyophilization, yielding "acetalated dextran" (Ac-DEX) (1.07 g) as a fine white powder. IR (KBr, $cm^{-1}$): 3444, 2989, 2938, 1381, 1231, 1176, 1053, 853. $^1$H NMR (400 MHz, $CDCl_3$): δ 1.39 (s, br, 25H), 3.25 (br, 6H), 3.45 (br, 2H), 3.60-4.15 (br, 12H), 4.92 (br, 1H), 5.13 (br, 1H).

2) Ethoxyacetal Modified Dextran.

If the generation of methanol on degradation must be strictly avoided, modification using 2-ethoxypropene rather than 2-methoxypropene can be carried out. Preparation of ethoxyacetal modified dextran is carried out in the same manner as the preparation of Ac-DEX using 2-ethoxypropene in place of 2-methoxypropene.

3) FITC-Dextran

Fluorescein isothiocyanate (FITC) modified dextran was acetalated in the same manner as described above except FITC-dextran ($M_w$=66100 g/mol, 10 mg fluorescein/g dextran) was substituted for dextran.

4) Alkyne Modified Dextran

Dextran bearing pendant alkyne groups ($M_w$=10500 g/mol, approximately 6 alkyne groups per 100 glucose repeat units) was acetalated in the same manner as described above except alkyne-modified dextran was used in place of dextran. Alkyne-modified dextran was prepared according to the procedure reported by De Geest et al., *Chem Commun (Camb)* 2008, 190-2.

5) Mannan

Mannan, a homopolysaccharide of mannose was acetalated in the same manner as described above for dextran except mannan ($M_w$=30000-70000 g/mol, from *Saccharomyces cerevisiae*) was used in place of dextran, the volume of DMSO was doubled, and the reaction was quenched after 20 h.

6) Maltodextrin

Maltodextrin, a homopolysaccharide of glucose was acetalated in the same manner as described above for dextran except maltodextrin ($M_w$=2300-4100 g/mol, from potato starch) was used in place of dextran.

7) Polyvinyl Alcohol

Polyvinyl alcohol (PVA, $M_w$=13000-23000 g/mol, 87-89% hydrolyzed) was acetalated in the same manner as described above for dextran except PVA was used in place of dextran, the volume of DMSO was increased 10 fold, the amount of 2-methoxypropene was reduced to 2.5 equivalents per monomer repeat unit, and the reaction was quenched after 15 min.

8) THP Modified Dextran

A flame-dried flask was charged with dextran ($M_w$=10, 500 g/mol, 300 mg, 0.029 mmol) and purged with dry $N_2$. Anhydrous DMSO (3 mL) was added and the resulting mixture was stirred until complete dissolution of the dextran was observed. Dihydropyran (3.4 mL, 37 mmol) was added followed by pyridiniump-toluenesulfonate (4.7 mg, 0.019 mmol). After stirring overnight the modified dextran was precipitated in dd-$H_2O$ (100 mL, pH 8). The product was isolated by centrifugation at 14800×g for 15 min and the resulting pellet was washed with dd-$H_2O$ (30 mL, pH 8) by vortexing and sonication followed by centrifugation and removal of the supernatant. Residual water was removed by lyophilization to yield the product (357 mg) as a coarse white powder.

9) Benzylidene Acetal Modified Dextran

A flame-dried flask was charged with dextran ($M_w$=10, 500 g/mol, 250 mg, 0.024 mmol) and purged with dry $N_2$. Anhydrous DMSO (4 mL) was added and the resulting mixture was stirred until complete dissolution of the dextran was observed. Benzaldehyde dimethyl acetal (0.35 mL, 2.3 mmol) was added followed by 5 Å molecular sieves (5 g) and p-toluenesulfonic acid monohydrate (15 mg, 0.08 mmol). After stirring for 22 h the reaction was quenched with TEA (0.15 mL, 1.1 mmol), the sieves were removed by filtration and the modified dextran was precipitated in dd-$H_2O$ (125 mL, pH 8). The product was isolated by centrifugation at 14800×g for 15 min and the resulting pellet was washed with dd-$H_2O$ (50 mL, pH 8) by vortexing and sonication followed by centrifugation and removal of the supernatant. Residual water was removed by lyophilization to yield the product (249 mg) as a fine white powder.

Example 4

Preparation of Modified Polyhydroxylated Polymer Particles

Preparation of Double Emulsion Particles Containing OVA.

Microparticles containing ovalbumin (OVA) were made using a double emulsion water/oil/water (w/o/w) evaporation method similar to that described by Bilati et al. (Yolles, S.; Leafe, T. D.; Meyer, F. J., *J. Pharm. Sci.* 1975, 64, 115-6). Briefly, OVA (10 mg) was dissolved in phosphate buffered saline (PBS, 137 mM NaCl, 10 mM phosphate, 2.7 mM KCl, pH 7.4, 50 µl). Ac-DEX (200 mg) was dissolved in $CH_2Cl_2$ (1 mL) and added to the OVA solution. This mixture was then emulsified by sonicating for 30 s on ice using a probe sonicator (Branson Sonifier 450) with an output setting of 3 and a duty cycle of 10%. This primary emulsion was added to an aqueous solution of poly(vinyl alcohol) (PVA, $M_w$=13 000-23 000 g/mol, 87-89% hydrolyzed) (2 mL, 3% w/w in PBS) and sonicated for an additional 30 s on ice using the same settings. The resulting double emulsion was immediately poured into a second PVA solution (10 ml, 0.3% w/w in PBS) and stirred for 3 h allowing the organic solvent to evaporate. The particles were isolated by centrifugation (14 800×g, 15 min) and washed with PBS (50 mL) and dd-$H_2O$ (2×50 mL, pH 8) by vortexing and sonication followed by centrifugation and removal of the supernatant. The washed particles were resuspended in dd-$H_2O$ (2 mL, pH 8) and lyophilized to yield a white fluffy solid (135 mg).

Preparation of Empty Double Emulsion Particles.

Particles that did not contain protein were made in the same manner as above omitting OVA.

Preparation of Empty PLGA Particles.

Particles prepared from poly(DL-lactide-co-glycolide) (PLGA, 85% lactide, 15% glycolide) were made in the same manner as above substituting PLGA for Ac-DEX.

Preparation of Double Emulsion Particles Containing FITC-Dextran.

Particles containing fluorescein isothiocyanate (FITC) labeled dextran were made in the same manner as above substituting FITC-dextran ($M_w$=66 100 g/mol, 10 mg) for OVA.

Quantification of Encapsulated OVA.

Ac-DEX particles containing OVA were suspended at a concentration of 2 mg/mL in a 0.3 M acetate buffer (pH 5.0) and incubated at 37° C. under gentle agitation for 3 d using a Thermomixer R heating block (Eppendorf). After the particles had been fully degraded, aliquots were taken and analyzed for protein content using the fluorescamine reagent and a microplate assay as described by Lorenzen et al. (Heller, J., *Ann. N. Y. Acad. Sci.* 1985, 446, 51-66). Empty Ac-DEX particles were degraded in a similar fashion and used to determine a background fluorescence level. The results were compared to a standard curve and the mass of OVA encapsulated was calculated. The protein loading was 3.7±0.4 wt % and the loading efficiency was 74%.

Single Emulsion Particle Preparation.

Single emulsion particles encapsulating pyrene were prepared according to a procedure adapted from Jung et al. (Rosen, H. B.; Chang, J.; Wnek, G. E.; Linhardt, R. J.; Langer, R., *Biomaterials* 1983, 4, 131-3). Briefly, Ac-DEX (49.9 mg) and pyrene (5.5 mg) were dissolved in $CH_2Cl_2$ (1 mL). This solution was added to a PVA solution (3 mL, 1% w/w in PBS) and emulsified by sonicating for 30 s on ice using a probe sonicator (Branson Sonifier 450) with an output setting of 5 and a duty cycle of 70%. The resulting emulsion was poured into a second PVA solution (50 ml, 0.3% w/w in PBS) and stirred for 4 h allowing the organic solvent to evaporate. The single emulsion particles were isolated in the same manner as described for the double emulsion particles above. The washed particles were resuspended in dd-H2O (2 mL, pH 8) and lyophilized to yield a white fluffy solid (38 mg).

Quantification of Encapsulated Pyrene.

The amount of encapsulated pyrene in single emulsion microparticles was determined by measuring pyrene's absorbance at 335 nm. Ac-DEX particles were weighed out in triplicate and dissolved in THF by sonicating the solutions for 2 min. The resulting solutions were diluted and the absorbance at 335 nm was determined. The loading of pyrene in the particles was calculated using pyrene's molar absorptivity in THF as reported by Venkataramana et al. (Solbrig, C. M.; Saucier-Sawyer, J. K.; Cody, V.; Saltzman, W. M.; Hanlon, D. J., *Mol. Pharm.* 2007, 4, 47-57). The pyrene loading was 3.6±0.5 wt % and the loading efficiency was 36%.

Scanning Electron Microscopy.

Microparticles were characterized by scanning electron microscopy using a S-5000 microscope (Hitachi, Japan). Particles were suspended in dd-$H_2O$ (pH 8) at a concentration of 1 mg/mL and the resulting dispersions were dripped onto silicon wafers. After 15 min, the remaining water was wicked away using tissue paper and the samples were allowed to air dry. The particles were then sputter coated with a 2 nm layer of a palladium/gold alloy and imaged. An SEM image of single emulsion particles is presented in FIG. 12C.

Particle Size Analysis by Dynamic Light Scattering.

Particle size distributions and average particle diameters were determined by dynamic light scattering using a Nano ZS (Malvern Instruments, United Kingdom). Particles were suspended in dd-$H_2O$ (pH 8) at a concentration of 1 mg/mL and three measurements were taken of the resulting dispersions. Size distribution histograms are presented in FIG. 16.

Example 5

Characterization of Polymers and their Degradation Products

Particle Degradation: Detection of Soluble Polysaccharides Via BCA Assay.

Figure 2:
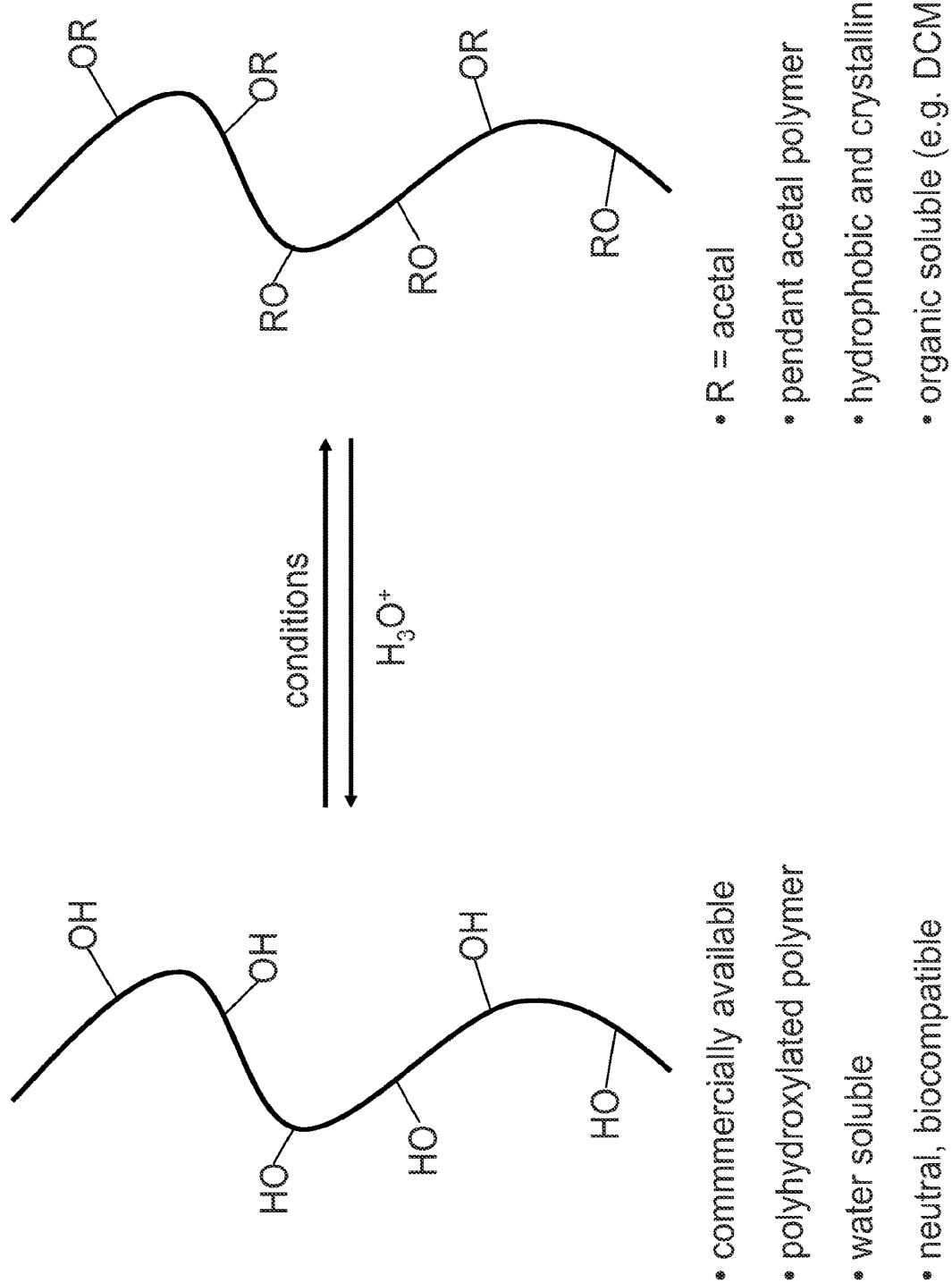
FIG. 2 shows a general synthetic scheme for the preparation of modified polyhydroxylated polymers.
Figure 3:
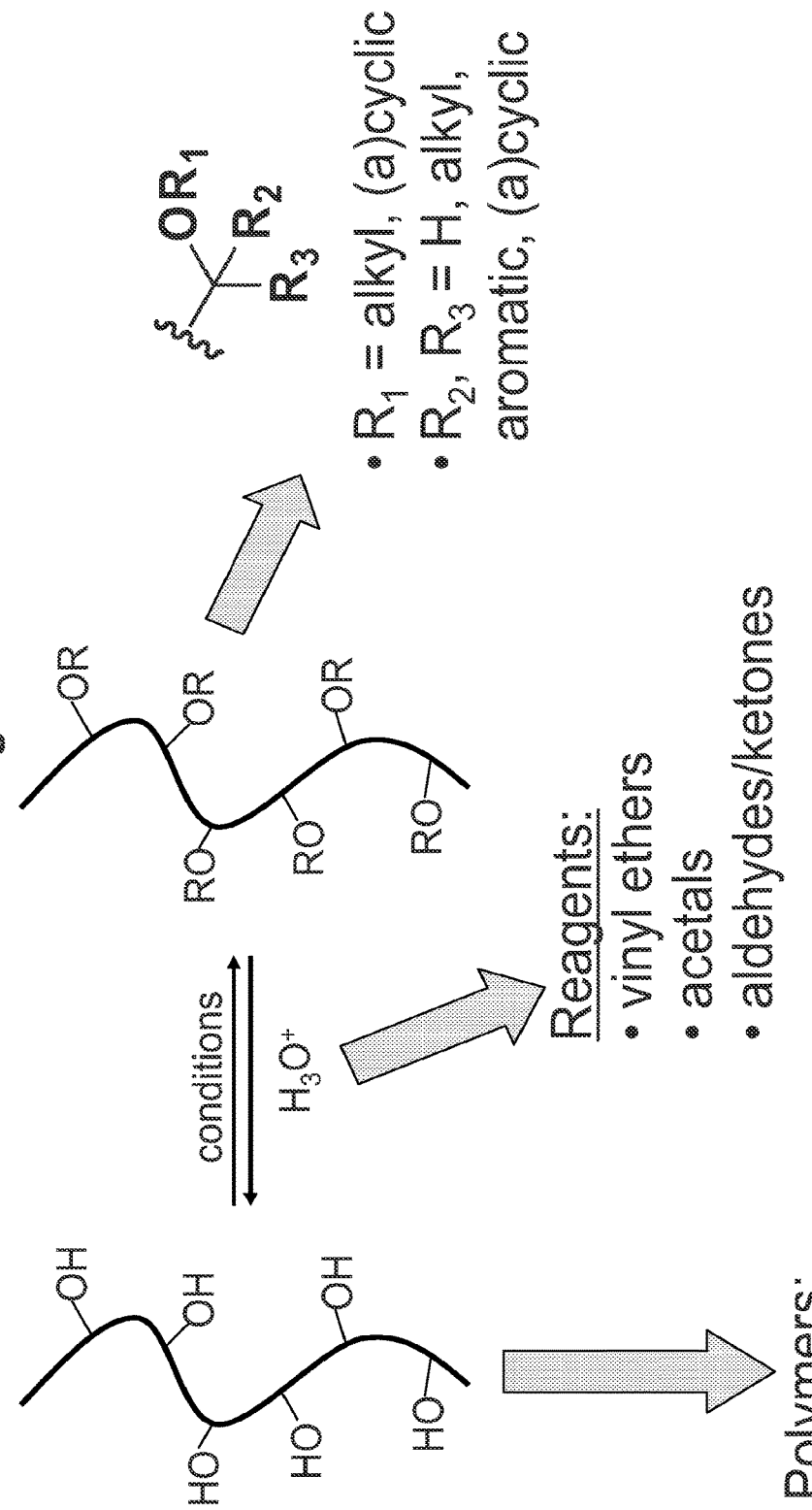
FIG. 3 shows an overall synthetic scheme for the preparation of modified polyhydroxylated polymers.

Empty Ac-DEX particles were suspended in triplicate at a concentration of 2 mg/mL in either a 0.3 M acetate buffer (pH 5.0) or PBS (pH 7.4) and incubated at 37° C. under gentle agitation using a Thermomixer R heating block (Eppendorf). At various time points, 120 μl aliquots were removed, centrifuged at 14 000×g for 10 min to pellet out insoluble materials and the supernatant was stored at −20° C. The collected supernatant samples were analyzed for the presence of reducing polysaccharides using a microplate reductometric bicinchoninic acid based assay according to the manufacturer's protocol (Micro BCA Protein Assay Kit, Pierce, USA; FIG. 2a). (Gvili, K.; Benny, O.; Danino, D.; Machluf, M., *Biopolymers* 2007, 85, 379-91).

pH-Dependant Release of FITC-Dextran from Ac-DEX Particles.

This experiment was performed essentially in the same manner as above except FITC-dextran loaded particles were used instead of empty particles. The quantity of FITC-dextran in the supernatant samples was determined by measuring the emission at 515 nm with an excitation of 490 nm. The amount of FITC-dextran in each sample was calculated by fitting the emission to a calibration curve. The results of this experiment are presented in FIG. 17.

Particle Degradation: $^1$H NMR Study.

Empty Ac-DEX particles (9.5 mg) and deuterated PBS buffer (850 μL, pH 5.5) were added to an NMR tube, which was immediately flame sealed. An $^1$H NMR spectrum was taken (initial time point) and the tube was placed in an oil bath heated to 37° C. After various time points additional $^1$H NMR spectra were taken and the appearance of acetone, methanol, and signals assigned to the methyl groups of cyclic isopropylidene acetals (Sengupta, S.; Eavarone, D.; Capila, I.; Zhao, G. L.; Watson, N.; Kiziltepe, T.; Sasisekharan, R., *Nature* 2005, 436, 568-572) was measured as a ratio of these peaks' integral to the integral of the internal standard peak (3-(trimethylsilyl) propionic-2,2,3,3, $d_4$ acid, sodium salt). The data was normalized by dividing the values for acetone and the cyclic acetals by six and the values for methanol by three. A stack plot of the NMR spectra at various time points is presented in FIG. 18 and spectrum of the final time point, which shows signals only from dextran, methanol and acetone is presented in FIG. 19.

Particle Degradation: Digital Photography.

Empty Ac-DEX particles were suspended at a concentration of 2 mg/mL in either a 0.3 M acetate buffer (pH 5.0) or PBS (pH 7.4) and incubated at 37° C. under gentle stirring. Digital photographs of the samples were obtained after various time points. The white object visible in some of the vials is a magnetic stir bar.

Example 6

Control of Degradation Rate of Acetalated Dextran

Figure 13:
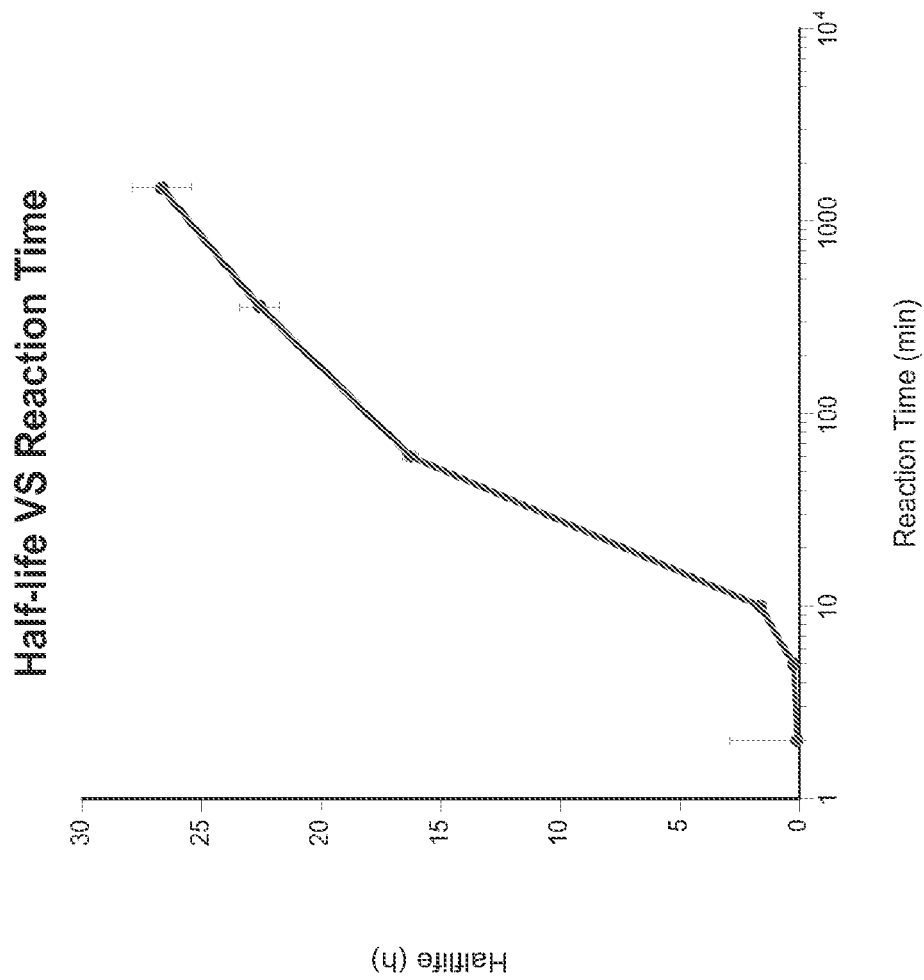

By changing the amount of time the dextran was acetalated, the degradation rate of the resulting polymer could be tuned over a 200-fold range (FIG. 13).

Degradation was observed using the BCA assay. The tabulated values (in hours) are as follows.

TABLE 2

Degradation over time at pH 5 or pH 7.4.

| | pH 5 | pH 7.4 |
|---|---|---|
| 2 min | 0.13 | 27.9 |
| 5 min | 0.27 | 75.6 |
| 10 min | 1.7 | 425 |
| 60 min | 16.3 | 4075 |
| 360 min | 22.6 | 5650 |
| 1485 min | 26.7 | 6675 |

No degradation was observed after 48 hours for the slower degrading particles at pH 7.4, so it was not possible to accurately calculate a half-life for them. The values in gray (col pH 7.4, 10 min-1485 min) are expected values based on the difference in proton concentration associated with the different pHs Example 7

Class I Antigen Presentation Assays

In one embodiment, particles prepared from these acid degradable acetal-derivatized dextran polymers are designed to release their bioactive material payload into the cytoplasm of cells upon lysosomal destabilization. Higher loading capacity of the particles may also lead to greater antigen presentation of the encapsulated bioactive material.

The LacZ MHC Class I antigen presentation assay, as described by Sanderson, S.; Shastri, N. in *Inter. Immun.* 1994, 6, 369-376, is performed with degradable polymer particles made according to Example 3 with the modified hydroxylated polymers of Example 2 to test their ability to deliver proteins into APCs for Class I antigen presentation. This experiment uses the LacZ B3Z hybridoma, which is a CTL that recognizes the peptide sequence, SIINFEKL (SEQ ID NO: 8), from ovalbumin, complexed with the MHC Class I molecule H-2K$^b$. This hybridoma produces β-galactosidase after encountering APCs that present SIINFEKL as a Class I antigen, thus allowing Class I antigen presentation to be quantified by measuring β-galactosidase activity.

A proper control would be to compare the amount presented by the particles when incubated with the SIINFEKL peptide (SEQ ID NO: 8), which is directly displayed on the antigen presenting cells and not delivered to the cytoplasm of the cells first. In a preferred embodiment, the bioactive loading capacity and efficiency should lead to an absorbance of that is equal to the saturation absorbance of the SIINFEKL peptide (SEQ ID NO: 8), control using the antigen presentation assay described by Sanderson, S.; Shastri, N. in *Inter. Immun.* 1994, 6, 369-376.

Figure 15:
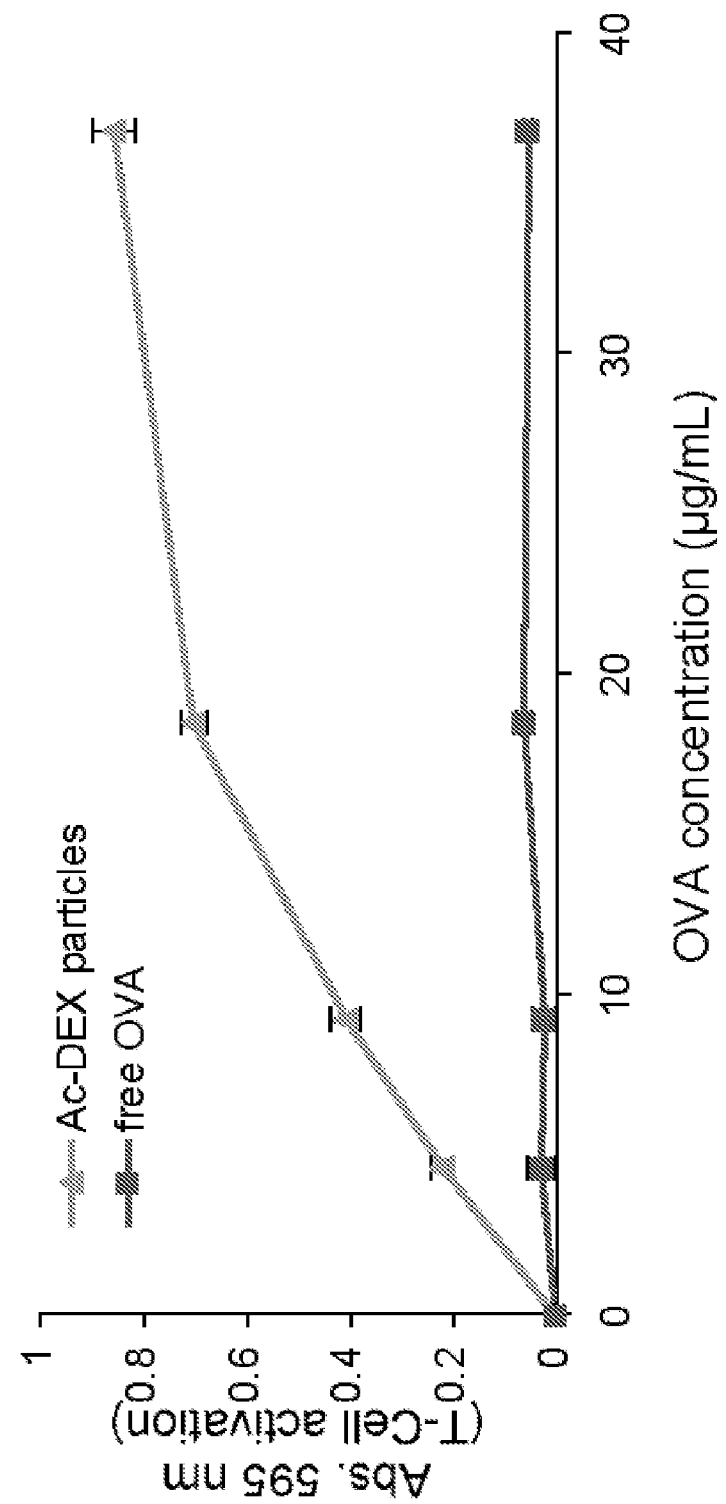
FIG. 15 shows a graph of the results of the B3Z assay measuring antigen presentation of RAW macrophages pulsed with free OVA or Ac-DEX particles encapsulating OVA.

The results of the Class I antigen presentation assay should showed that greater T-cell activation is seen for albumin loaded particles vs. free protein. APCs incubated with free ovalbumin are not able to activate CTLs, indicating that these APCs are unable to present free ovalbumin as a Class I antigen. This is presumably because ovalbumin endocytosed by the APCs, is sequestered in lysosomes, and does not have access to the APC cytoplasm. In contrast, APCs incubated with ovalbumin encapsulated in the degradable particles, can efficiently activate CTLs. Ovalbumin encapsulated in the degradable particles was orders of magnitude more efficient than free ovalbumin at inducing the activation of CTLs Thus the acid degradable particles were capable of delivering protein antigens into APCs for Class I antigen presentation (FIG. 15).

Higher protein loading in the degradable particles is expected to lead to an increase in antigen presentation.

In order to assess the feasibility of using Ac-DEX based materials for vaccine applications, OVA-loaded Ac-DEX particles were incubated with RAW macrophages. B3Z cells, a CD8$^+$ T-cell hybridoma engineered to secrete β-galactosidase when its T-cell receptor engages an OVA$_{257-264}$: K$_b$ complex, (Matsumoto, A.; Matsukawa, Y.; Suzuki, T.; Yoshino, H., *J. Control Release* 2005, 106, 172-80), were maintained in RPMI 1640 (Invitrogen, USA) supplemented with 10% fetal bovine serum, 2 mM Glutamax, 50 mM 2-mercaptoethanol, 1 mM sodium pyruvate, 100 U/ml penicillin and 100 mg/ml streptomycin. $1 \times 10^4$ RAW macrophages were seeded overnight in a 96 well plate and subsequently incubated with OVA-containing Ac-DEX particles or free OVA. After 6 h, the cells were washed and $1 \times 10^5$ B3Z cells were added to the macrophages and cocultured for an additional 16 h. The medium was removed and 100 of CPRG buffer (91 mg of chlorophenol red b-D-galactopyranoside (CPRG, Roche, USA), 1.25 mg of NP40 (EMD Sciences, USA), and 9 ml of 1 M MgCl$_2$ in 1 L of PBS) was added to each well. After six hours of incubation, Ac-DEX particles increased MHC class I presentation of the OVA-derived CD8$^+$ T-cell epitope, SIINFEKL, by a factor of 16 relative to free OVA (FIG. 15) measured by the B3Z assay (Karttunen, J.; Shastri, N., *Proc. Natl. Acad. Sci. U.S.A* 1991, 88, 3972-6). This drastic increase in presentation indicates that these particles may be promising materials for vaccines against tumors and certain viruses, where MHC-I presentation is crucial for the activation and proliferation of CD8$^+$ T-cells.

Example 8

Examples of Encapsulation of Hydrophobic and Hydrophilic Cargoes in Particles Made from Acetalated Polymers
1) Ovalbumin Encapsulation Microparticles containing ovalbumin (OVA) were made using a double emulsion water/oil/water (w/o/w) evaporation method similar to that described by Bilati et al., *Pharm. Dev. Technol.* 2003, 8, 1-9. Briefly, OVA (10 mg) was dissolved in phosphate buffered saline (PBS, 137 mM NaCl, 10 mM phosphate, 2.7 mM KCl, pH 7.4, 50 µl). Ac-Dex (200 mg) was dissolved in CH$_2$Cl$_2$ (1 mL) and added to the OVA solution. This mixture was then emulsified by sonicating for 30 s on ice using a probe sonicator (Branson Sonifier 450) with an output setting of 3 and a duty cycle of 10%. This primary emulsion was added to an aqueous solution of poly(vinyl alcohol) (PVA, M$_w$=13000-23000 g/mol, 87-89% hydrolyzed) (2 mL, 3% w/w in PBS) and sonicated for an additional 30 s on ice using the same settings. The resulting double emulsion was immediately poured into a second PVA solution (10 ml, 0.3% w/w in PBS) and stirred for 3 h allowing the organic solvent to evaporate. The particles were isolated by centrifugation (14800×g, 15 min) and washed with PBS (50 mL) and dd-H$_2$O (2×50 mL, pH 8) by vortexing and sonication followed by centrifugation and removal of the supernatant. The washed particles were resuspended in dd-H$_2$O (2 mL, pH 8) and lyophilized to yield a white fluffy solid (135 mg).
2) siRNA Encapsulation Double emulsion particles containing siRNA were prepared as follows: siRNA (40 nmol) was dissolved in IDTE (pH 7.5, 50 Ac-Dex (50 mg) was dissolved in CH$_2$Cl$_2$ (0.6 mL). DOTAP (400 µL of a 25 mg/mL solution in chloroform) was added to the Ac-DEX solution (20% DOTAP). The DOTAP/Ac-DEX solution was added to the siRNA solution. This mixture was then emulsified by sonicating for 30 s on ice using a probe sonicator (Branson Sonifier 450) with an output setting of 5 and a duty cycle of 80%. This primary emulsion was then added to an aqueous solution of poly(vinyl alcohol) (PVA, $M_w$=13000-23000 g/mol, 87-89% hydrolyzed) (2 mL, 3% w/w in PBS) and sonicated for an additional 30 s on ice using the same settings. The resulting double emulsion was immediately poured into a second PVA solution (10 mL, 0.3% w/w in PBS) and stirred for 3 h allowing the organic solvent to evaporate. The particles were isolated by centrifugation (14800×g, 15 min) and washed with PBS (50 mL) and dd-$H_2O$ (2×50 mL, pH 8) by vortexing and sonication followed by centrifugation and removal of the supernatant. The washed particles were resuspended in dd-$H_2O$ (2 mL, pH 8) and lyophilized to yield a white fluffy solid.

3) Simultaneous Ovalbumin and Imiquimod Encapsulation

Microparticles containing both the hydrophilic macromolecule OVA and the hydrophobic small molecule imiquimod were prepared in the same fashion as particles containing only OVA except that the $CH_2Cl_2$ was replaced with $CHCl_3$ containing 2 mg/mL imiquimod.

4) FITC-Dextran Encapsulation

Particles containing fluorescein isothiocyanate (FITC) labeled dextran were made in the same manner as above substituting FITC-dextran ($M_w$=66100 g/mol, 10 mg) for OVA.

5) Plasmid Encapsulation

Plasmid-loaded Microparticles were made using a modified double emulsion water/oil/water evaporation method. Ac-DEX (40 mg) and a poly(β-aminoester) polymer (10 mg) were dissolved in ice-cold $CH_2Cl_2$ (1 mL). Plasmid DNA encoding firefly luciferase reporter protein, gWIZ Luciferase, was purchased from Aldevron/Genlantis (USA) and was dissolved in TE buffer (10 mM Tris, 1 mM EDTA, pH 8.5) at a concentration of 5 mg/mL. The plasmid solution (100 μL) was added to the polymer solution and the mixture was emulsified by sonicating for 5 s using a Branson Sonifier 450 sonicator with a microtip probe, an output setting of 1, and a continuous duty cycle. This primary emulsion was added to an ice-cold aqueous solution of PVA (20 mL, 3% w/w in PBS) and homogenized for 30 s at 10,000 rpm using an IKA T-25 Ultra-Turrax digital homogenizer with an S25N-10G generator. The resulting double emulsion was immediately poured into a second PVA solution (40 mL, 0.3% w/w in PBS) and stirred for 2 h allowing the organic solvent to evaporate. The particles were isolated by centrifugation (3,000×g, 5 min) and washed with PBS (1×20 mL) and dd-$H_2O$ (2×20 mL, pH 8). The washed particles were resuspended in dd-$H_2O$ (2 mL, pH 8) and lyophilized to yield a white fluffy solid (34 mg). (2 mL, pH 8) and lyophilized to yield a white fluffy solid (135 mg).

6) Preparation of Particles from Acetalated Mannan

Figure 10:
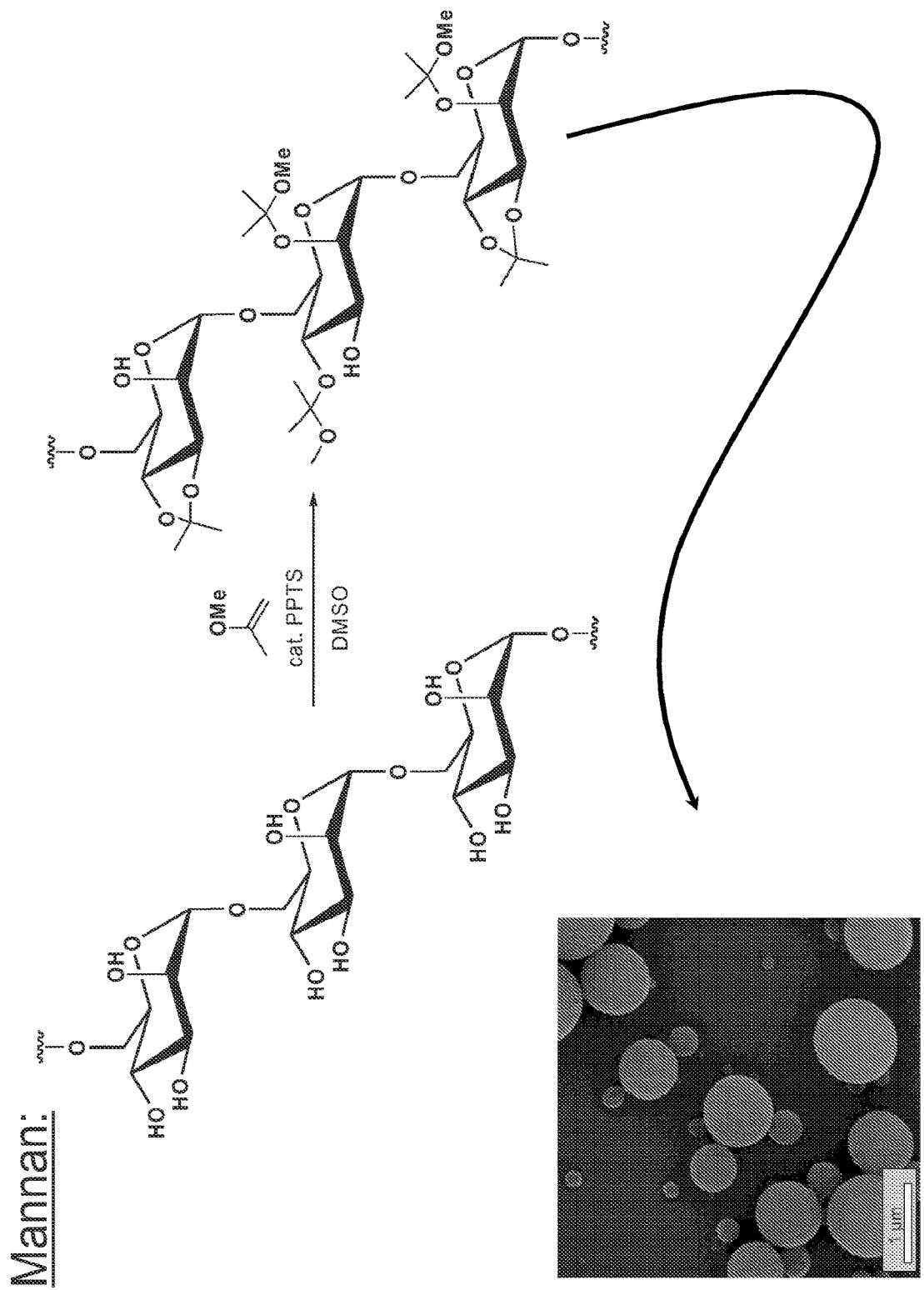
FIG. 10 shows the scheme for the synthesis of mannan modified to mannan having cyclic and acyclic ketals masking the hydroxyl groups and an SEM of particles formed by a solvent-evaporation-based technique (scale bar is 1 μm).
Figure 11:
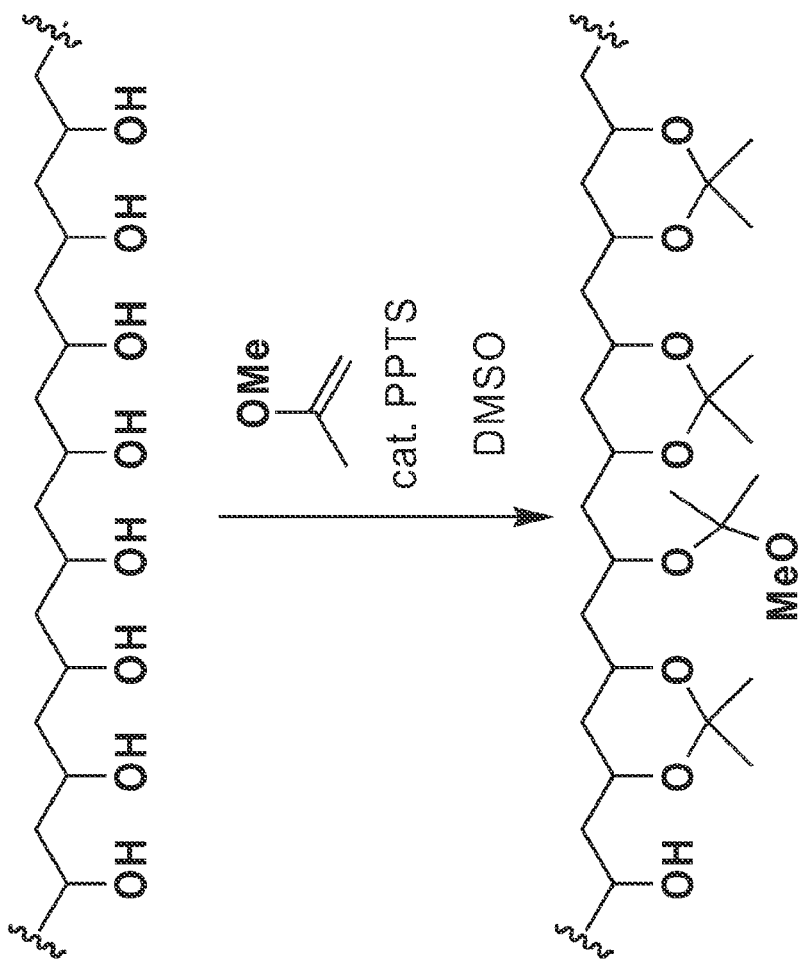
FIG. 11 shows the synthetic scheme of acetalated polyvinyl alcohol using 2-methoxypropene, pyridinium-p-toluenesulfonate, DMSO.

Particles made from acetalated mannan were prepared as described above substituting acetalated mannan for acetalated dextran and omitting the OVA solution and the first emulsion step (see FIG. 10).

7) Pyrene Encapsulation

Single emulsion particles encapsulating pyrene were prepared according to a procedure adapted from Jung et al. (Jung, J.; Lee, I. H.; Lee, E.; Park, J.; Jon, S., *Biomacromolecules* 2007, 8, 3401-3407). Briefly, Ac-Dex (49.9 mg) and pyrene (5.5 mg) were dissolved in $CH_2Cl_2$ (1 mL). This solution was added to a PVA solution (3 mL, 1% w/w in PBS) and emulsified by sonicating for 30 s on ice using a probe sonicator (Branson Sonifier 450) with an output setting of 5 and a duty cycle of 70%. The resulting emulsion was poured into a second PVA solution (50 mL, 0.3% w/w in PBS) and stirred for 4 h allowing the organic solvent to evaporate. The single emulsion particles were isolated in the same manner as described for the double emulsion particles above.

8) Imiquimod Encapsulation

Single emulsion particles encapsulating imiquimod were prepared according to the same procedure used to encapsulate pyrene, but $CHCl_3$ was used in place of $CH_2Cl_2$ and imiquimod was used in place of pyrene. The single emulsion particles were isolated in the same manner as described for the double emulsion particles above.

9) Doxorubicin Encapsulation

Single emulsion particles encapsulating doxorubicin (Dox) were prepared according to a procedure adapted from Tewes et al. (Tewes, F.; Munnier, E.; Antoon, B.; Ngaboni Okassa, L.; Cohen-Jonathan, S.; Marchais, H.; Douziech-Eyrolles, L.; Souce, M.; Dubois, P.; Chourpa, I., *Eur J Pharm Biopharm* 2007, 66, 488-92). Briefly, Dox (1 mg) was dissolved in a sodium borate buffer (2 ml, 50 mM, pH 8.8) and mixed extensively overnight with $CH_2Cl_2$. The $CH_2Cl_2$ was then isolated and evaporated to a final volume of 1 mL. A solution of Ac-Dex (100 mg) in $CH_2Cl_2$ (1 mL) was added to the Dox. The resulting solution was added to a PVA solution (4 mL, 3% w/w in PBS) and emulsified by sonicating for 60 cycles on ice using a probe sonicator (Branson Sonifier 450) with an output setting of 4 and a duty cycle of 10%. The resulting emulsion was poured into a second PVA solution (10 mL, 0.3% w/w in PBS) and stirred for 4 h allowing the organic solvent to evaporate. The resulting particles were isolated in the same manner as described for the double emulsion particles above.

10) Encapsulation of Camptothecin by Nanoprecipitation

Ac-DEX particles can encapsulate organic molecules using noprecipitation. Camptothecin (2.4 mg) was dissolved in hot DMF (400 μL) then diluted with acetone (600 μL) containing Ac-Dex (100 mg). This solution was added dropwise to $H_2O$ (10 mL, pH 8). Particles were isolated by concentration using Centricon spin filters. Dry state storage could be obtained by lyophilization in the presence of 10% sucrose as a cryoprotectant.

Example 9

Toxicity of Degradable Particles.

The toxicity of bioactive material loaded degradable particles can be measured with the yellow tetrazolium salt, 3-(4,5-dimethylthiazolyl-2)-2,5-diphenyltetrazolium bromide (MTT), assay using RAW 309.CR1 macrophage cells (ATCC No. TIB-69, American Type Culture Collection, Manassas, Va.). The cells are incubated with the degradable particles in DMEM media with 10% F.B.S. The degradable particles are aspirated from the cells and then washed several times with PBS and allowed to grow for 24-48 hours. The cell viability is determined by measuring the absorbance of the reduced MTT reagent using the protocol described in Freshney et al. (Freshney, I. R. (1994) *Culture of animal cells*, Wiley-Liss, Inc, New York, N.Y.) as compared to a control. MTT (yellow) is reduced metabolically by healthy cells in part by the action of dehydrogenase enzymes in mitochondria, to generate purple formazan crystals, which are solubilized by the addition of a detergent and the absorbance is measured at 570 nm. Thus, the measurement of the ability of cells to reduce the MTT reagent metabolically is a measurement of the health of the cell population.

RAW 309.CR1 macrophage cells are split at $5\times10^4$ cells per well in a 96 well plate and allowed to grow overnight.

The cells are then incubated with the degradable particles with variable amounts of loaded ovalbumin for 24 hours in DMEM media with 10% F.B.S. The degradable particles are then aspirated from the cells, and then washed several times with PBS and allowed to grow for another 24 hours.

The cell viability is determined by measuring the absorbance of the reduced MTT reagent. The MTT assay is performed using 0.5, 1, 2.5 and 5 mg particles/mL serum in each well with a particle loading of 10 micrograms protein/mg particle. After 24 hours, number of viable cells remaining is observed. It is preferred that at least 50%, more preferably 80-90% viable cells remain. Thus, it can be found whether the degradable particles of the invention are not toxic to mammalian cells if more than 50% of the cells remain viable. For cell viability experiments, degradation products of empty Ac-DEX particles were tested using RAW macrophages (FIG. 20b). Additionally, empty Ac-DEX particles and empty PLGA particles were incubated with RAW macrophages (FIG. 20a). The degradation products were obtained by incubating Ac-DEX particles in a 0.3 M acetate buffer (pH 5.0) at 37° C. under gentle agitation for 3 d. The resulting solution was desalted using a Microcon 3 centrifugation filter (Millipore, USA) and lyophilized. During the desalting and lyophilization steps the methanol and acetone released during degradation was removed. Before use in the viability experiment, the lyophilized degradation products were dissolved in medium, and methanol and acetone were added corresponding to the maximum amount of these byproducts released, as found in the $^1$H-NMR degradation study described above.

For each viability experiment, $1 \times 10^4$ RAW macrophages were seeded in a 96 well plate and allowed to grow overnight. Serial dilutions of the degradation products, empty Ac-DEX or PLGA particles were added to the cells, which were then incubated overnight. The next morning, viability was measured using the MTT assay (described above). Results are presented as the mean of triplicate cultures±95% confidence intervals Although toxic in large quantities, the level of methanol released by Ac-DEX materials (~7 wt. %) would be below the EPA recommended limit of daily exposure as long as the dosage does not exceed 7 g/kg/day. If complete elimination of methanol becomes necessary, 2-ethoxypropene instead of 2-methoxypropene could be used.

Figure 20:
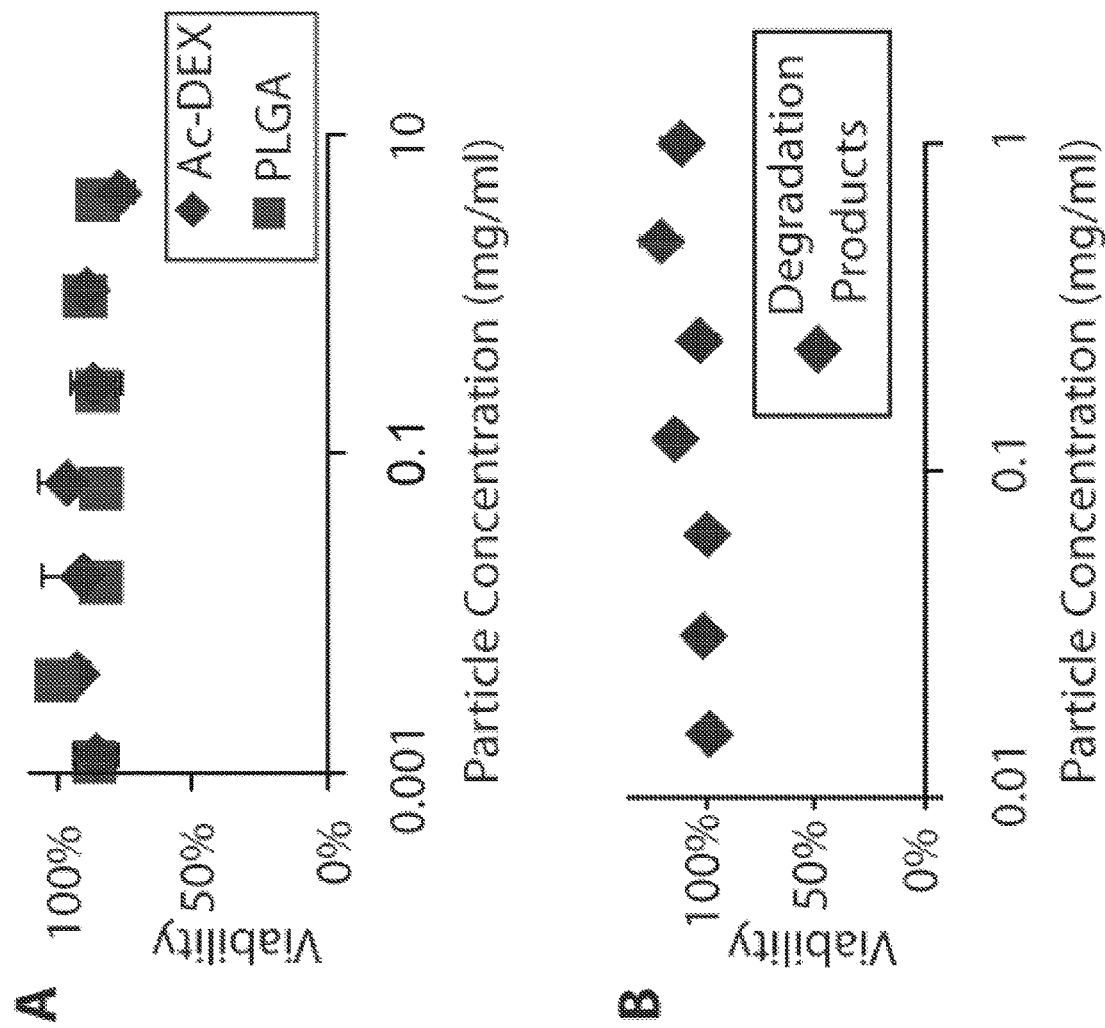
FIG. 20. Cell viability of RAW macrophages was measured by MTT assay after overnight culture with (a) Ac-DEX particles or PLGA particles or (b) Ac-DEX particle degradation products.

To assess the biocompatibility of Ac-DEX particles, we compared them to particles prepared from an FDA approved polymer, poly (lactic-co-glycolic acid). We found no significant difference in toxicity between the two materials in both HeLa cells and RAW macrophages. The degradation products of Ac-DEX particles were also found to be non-toxic (FIG. 20).

Example 10

Release of Bioactive Material from Degradable Polymer Particles

Degradable particles are made according to Example 4 with the degradable polymers in Example 1, encapsulating fluorescently labeled dextran and fed to macrophage cells and compared to non-degradable control particles. When a nondegradable particle is used, the fluorescence is more localized showing that when nondegradable particles have been taken up by the cells, they remain sequestered in the lysosome without a mechanism of release. When the acid degradable particles are used, the fluorescence is more diffuse within the cytoplasm of cells, which is indicative of cytoplasmic release of the degradable particle contents.

Example 11

In Vivo Studies to Assess the Degradable Polymer Particle Delivery of Vaccine Therapeutics to Antigen Presenting Cells To assess the ability of the acid-degradable protein-loaded particles to deliver protein to the cytoplasm of APCs and activate CTLs and provide a protective immunity in vivo, a preliminary tumor protection experiment is performed using the EG7 tumor model (El-Shami, K., Tirosh, B., Bar-Haim, E., Carmon, L., Vadai, E., Fridkin, M., Feldman, M., and Eisenbach, L. (1999) MHC class I-restricted epitope spreading in the context of tumor rejection following vaccination with a single immunodominant CTL epitope. *Eur. J. Immunol.* 29, 3295-3301; Kim, T. S., Chung, S. W., and Hwang, S. Y. (2000) Augmentation of antitumor immunity by genetically engineered fibroblast cells to express both B7.1 and interleukin-7. *Vaccine* 18, 2886-2894). EG7 is a derivative of the thymoma EL4, which was transfected with the ovalbumin gene, making it a target cell for CTLs activated against ovalbumin. The modified polyhydroxylated polymer chosen for in vivo study should demonstrate good dispersibility which may be an important consideration for the study if the particles must be suspended in saline and injected into animals. Certain modified polyhydroxylated polymers may be somewhat more difficult to suspend, most likely due to a degree of particle aggregation as a result of higher ovalbumin content.

Briefly, in an in vivo study, the modified polyhydroxylated particles are injected into the foot pad of CD4 or CD8 transgenic mice to show that the particles can activate cytotoxic T lymphocytes in vivo. More preferably, delivery is by injection of 50 μl of resuspended particle using a 25 gauge syringe in the flanks of these transgenic mice. At least 50 μg of OVA/mouse should suffice per injection with at least 3 mice per group injected. Also 150 μg of particles with OVA and a similar amount of particles used for control are injected. The lymph nodes are isolated 7 days after the injection and analyzed for antigen specific T cell priming.

In Vivo Tumor Protection Experiment.

Experiments are performed with female C57BL/6 mice and all immunizations are administered by subcutaneous injections using 26 gauge needles. There are three groups (15 mice per group): control mice injected with saline (200 μL); mice injected with free ovalbumin in saline (50 μg in 200 μL); and mice injected with ovalbumin encapsulated in particles dispersed in saline (1.13 mg particles, corresponds to 50 μg ovalbumin, in 200 μL). A second identical immunization is delivered 2 weeks after the first. Then 10 days after the second immunization, tumors are established by administering an injection of $1 \times 10^6$ EG7-OVA tumor cells in 100 μL saline into the shaved left flank of each mouse. One week prior to injection, the EG7 cells are stained with the anti-SIINFEKL/$K^b$ monoclonal antibody 25.D1-16 and the secondary goat anti-mouse antibody labeled with R-phycoethrin (PE). Then highly ovalbumin-expressing cells are collected using flourescence-activated cell sorting (FACS) and proliferated. After injection, the tumor growth is monitored by measuring two perpendicular axes using digital calipers. Tumor volume is then calculated using the equation, volume=0.5×length×width, with the length being the longest diameter and the width being the shortest diameter of the two perpendicular measurements. Once the tumor reaches 1.5 cm in average diameter, the mouse is removed from the experiment and euthanized according to guidelines set by the UC-Berkeley Animal Care and Use Committee. Mice are also removed if they showed other signs of pain or distress such as a lack of cleaning, eating, or mobility. A log rank test is used to determine p-values. A p-value of 0.05 or less is considered to be statistically significant.

In a previous experiment described in Standley et al., Acid-degradable particles for protein-based vaccines: enhanced survival rate for tumor-challenged mice using ovalbumin model, *Bioconjug Chem.* 2004 November-December; 15(6):1281-8, using polyacrylamide particles made with an acid-degradable crosslinker, mice injected showed slower tumor growth and 100% survival rate after 17 days. These encouraging preliminary results suggest that modified polyhydroxylated particles should stimulate an immune response against EG7 tumor cells and provide a protective immune response against tumor cells in vivo.

Future experiments can seek to take advantage of the synthetic flexibility of the presently described delivery system through incorporation of APC targeting and immunostimulatory groups such as mannose and CpG DNA into the present modified polyhydroxylated particles. Additional studies will also test samples with varied doses and protein loadings to determine if these variables have the same effect in vivo as they do in vitro.

Example 12

Tumor Immunotherapy with Model System

In one embodiment, Ac-DEX particles will encapsulate OVA similar to (Example 9 with B3Z assay) and be used in a tumor prophylactic and treatment vaccination against cancer. MO5 is a B16 tumor cell line that expresses OVA (Falo et al. 1995, Targeting antigen into the phagocytic pathway in vivo induces protective tumour immunity. Nat Med 1:649-53). Mice are immunized subcutaneously with 2 mg of Ac-DEX particles with a 2.5 wt % loading of OVA (50 μg of OVA) in the left flank on day 0. Other groups include mice which are injected with either OVA, saline, or Ac-DEX particles encapsulating OVA and an immunostimulatory CpG stimulant. We have shown earlier that adding CpG with acid labile particles drastically increases the efficacy of treatment (Standley et al. 2007, Incorporation of CpG oligonucleotide ligand into protein-loaded particle vaccines promotes antigen-specific CD8 T-cell immunity. Bioconjug Chem 18:77-83). CpG can be either co-injected with the particles, or it can be encapsulated inside the particles. On day 7 mice are challenged with 200,000 MO5 tumor cells that are implanted subcutaneously in the right flank After injection, the tumor growth is monitored by measuring two perpendicular axes using calipers. Tumor volume is then calculated using the equation, volume=0.5×length× width, with the length being the longest diameter and the width being the shortest diameter of the two perpendicular measurements. Once the tumor reaches 1.5 cm in average diameter, the mouse is removed from the experiment and euthanized according to guidelines set by the UC-Berkeley Animal Care and Use Committee. Mice are also removed if they show other signs of pain or distress such as a lack of cleaning, eating, or mobility. Mice injected with PBS and nonencapsulated OVA have the fastest tumor onset and tumor growth. Mice injected with OVA encapsulated in Ac-DEX particles have a delay in cancer onset and increase in survival time. Mice receiving encapsulated OVA and coencapsulated or coinjected CpG have the slowest tumor onset and the longest survival time.

After tumor prophylactic experiments, treatment experiments are performed. Mice are implanted with 200,000 MO5 tumor cells on day 0. After day 0, mice are immunized on day 6 with either saline, 50 micrograms of OVA, OVA encapsulated in Ac-DEX particles, or OVA encapsulated in Ac-DEX particles with coencapsulated or coinjected CpG. After injection mice are monitored for tumor growth. Tumors shrink and disappear after a coinjection of OVA and CpG in Ac-DEX particles.

Example 13

Tumor Immunotherapy with Clinically Relevant System

In another embodiment, Ac-DEX particles will encapsulate natural antigens inherent in the tumors against which are vaccinated. For instance, the mouse B16 tumor possess the antigen tyrosinase-related protein (TRP2), which is also present in many human melanoma tumors (Jerome et al. 2006, Cytotoxic T lymphocytes responding to low dose TRP2 antigen are induced against B16 melanoma by liposome-encapsulated TRP2 peptide and CpG DNA adjuvant. J Immunother 29:294-305). The recombinant form of TRP2 will be encapsulated in Ac-DEX particles similar to the experiments done with OVA. On day 0, mice are immunized in the left flank with 2 mg of particles that are 2.5 wt % (50 μg of TRP2). As with the OVA tumor experiment, other groups include immunization with saline, free TRP2, or TRP2 particles with coencapsulated or coinjected CpG. After vaccination, on day 7, 200,000 B16 tumor cells are implanted in the right flank and mice are monitored for tumor growth. Mice receiving encapsulated OVA and coencapsulated or coinjected CpG have the slowest tumor onset and the longest survival time.

After tumor prophylactic experiments, treatment experiments are performed. Mice are implanted with 200,000 MO5 tumor cells on day 0. After day 0, mice are immunized on day 6 with either saline, 50 micrograms of TRP2, TRP2 encapsulated in Ac-DEX particles, or TRP2 encapsulated in Ac-DEX particles and CpG. After injection mice are monitored for tumor growth. Tumors shrink and disappear after a coinjection of OVA and CpG in Ac-DEX particles.

Besides injection with recombinant TRP2, known immunodominant peptide sequences of TRP2, approximately seven to nine amino acids long, can be incorporated inside the Ac-DEX particles. Methods of incorporating the peptide inside the particles could be as simple as a double emulsion technique (Batanero et al. 2002, Biodegradable poly(DL-lactide glycolide) microparticles as a vehicle for allergen-specific vaccines: a study performed with Ole e 1, the main allergen of olive pollen. J Immunol Methods 259:87-94). Other methods familiar to those in the art can be used in incorporating small peptides inside the particles.

Example 14

Ac-DEX Particles for Delivery of Chemotherapeutic Agents

In one embodiment, Ac-DEX particles will encapsulate chemotherapeutic agents such as doxorubicin (DOX) inside the particles by using the method described above. In order for the particles to have a long circulation time in vivo, particles can be coated with polyethylene glycol (PEG). It is well known to those in the art that particles coated with PEG have increased blood circulation in vivo (Shenoy et al. 2005, Poly(ethylene oxide)-modified poly(beta-amino ester) nanoparticles as a pH-sensitive system for tumor-targeted delivery of hydrophobic drugs: part 2. In vivo distribution and tumor localization studies. Pharm Res 22:2107-14). We plan on coating particles with a Pluronic triblock polymer in which the polypropylene glycol unit is absorbed onto the Ac-DEX particles leaving the PEG chains free to cover the surface of the particles. If a higher pegylation is desired, the alkyne dextran particles described earlier could be conjugated to azide functionalized PEG chains.

To determine the maximum in vivo tolerated dose for the particles, a varying concentration of doses of 0 (PBS), 20, 40, and 60 mg/kg DOX equivalents are injected intravenously. The weights and general health of the mice are monitored until the ninth day after injection. Based on weight loss, the maximum injection of particles tolerated in mice is calculated. Once determined, mice are implanted subcutaneously with a B16 tumor. After 3 days mice are injected with PBS, free DOX, Ac-DEX particles encapsulating DOX, pegylated-Ac-DEX particles, or Doxcil (a commercially available doxorubicin/liposome conjugate). Mice are monitored for tumor growth. Once the tumor reaches an average diameter of 1.5 cm, the mice are sacrificed. Mice injected with PBS have the fastest tumor growth followed by, free Dox, Ac-DEX particles, Doxcil and finally PEGylated Ac-DEX particles.

Further experiments could be done encapsulating multiple chemotherapeutic drugs such as camptothecin, paxlitaxel, and cisplatnin in a single carrier construct.

Example 15

Bioengineering Scaffolding and Sutures

In another embodiment Ac-DEX polymer is used as a bioengineering scaffold. There are many methods in making tissue engineering scaffolds out of biodegradable polymers such as poly(lactic-co-glycolic acid) (PLGA). PLGA has been used to make sutures, macroscopic implantable disks, and tissue scaffolds. Since Ac-DEX particles are soluble in most of the organic solvents PLGA is soluble in, Ac-DEX can be used to replace PLGA in these applications that are known by those in the art. Alternatives for PLGA are needed because in certain in vivo applications, PLGA has been known to lower the local pH in and around the polymer (Shenderova et al. 1999, The acidic microclimate in poly(lactide-co-glycolide) microspheres stabilizes camptothecins. Pharm Res 16:241-8). One method in particular is the gas foaming/leaching process (Ennett et al. 2006, Temporally regulated delivery of VEGF in vitro and in vivo. J Biomed Mater Res A 79:176-84). Ac-DEX particles are combined with NaCl particles (diameter, 250-425 nm) and 1% (w/v) alginate solution. The alginate serves to increase protein incorporation and functions as a stabilizer. This mixture is lyophilized and pressed into a pellet using a Carver press. The scaffolds will then be placed under high pressure CO2 gas and allowed to equilibrate. The pressure will be rapidly returned to ambient conditions leading to a thermodynamic instability and causing the polymer to foam and create an interconnected structure around the NaCl. Both types of particles foam and fuse together to create the scaffold, and no distinct particles or microspheres are present in the scaffold after this processing. The NaCl is leached in a CaCl2 solution to create a macroporous structure.

Bioengineering scaffolds can be used to encapsulate growth factors for bones, blood vessels, cardiovascular tissue, nerve cells and other tissue systems. Growth factors such as vascular endothelial growth factor (VEGF) can be incorporated in the Ac-DEX particles. Incorporation of VEGF inside the scaffold can increase blood vascular growth and an increase in vascularization (Sun et al. 2005, Sustained vascular endothelial growth factor delivery enhances angiogenesis and perfusion in ischemic hind limb. Pharm Res 22:1110-6).

Another application where Ac-DEX may be an advantageous replacement for PLGA is absorbable sutures. Sutures are prepared using methods known to those familiar with the art. Ac-DEX sutures are found to have tensile strength that is comparable to that of PLGA closure and sufficient flexibility for use. Rate of absorption is adjusted according to the needs of the wound closure. Generally, Ac-DEX sutures are appropriate for situations where absorption must occur faster than occurs with PLGA sutures or in situations where it is desirable to avoid local acidification from PLGA degradation.

Example 16

Gene Delivery Using Modified Hydroxylated Polymers

An embodiment for the use of Ac-DEX polymer, is the encapsulation of DNA inside Ac-DEX particles. Plasmid DNA was encapsulated into Ac-DEX using a double emulsion technique (Gwak and Kim, 2008, Poly(lactic-co-glycolic acid) nanosphere as a vehicle for gene delivery to human cord blood-derived mesenchymal stem cells: comparison with polyethylenimine. Biotechnol Lett). Briefly, 1 ml of luciferase plasmid DNA (pCMV-Luc, 2 mg/ml) in Tris/EDTA buffer was emulsified in 2 ml Ac-DEX solution (5% w/v in methylene chloride) with a probe sonicator for 1 min. The water-in-oil emulsion was further emulsified in 25 ml of a 2% (w/v) PBS buffered aqueous solution of polyvinyl alcohol using a homogenizer for an additional minute. The emulsion was stirred for 8 h at room temperature to remove the methylene chloride. The nanospheres were recovered by centrifugation at 12,000 g for 15 min at 4° C. The remaining pellet was resuspended in distilled water (with one drop of triethylamide) by vortexing and washed five times with distilled water to remove PVA and unentrapped agent. The washings were performed by centrifugation at 12,000 g for 15 min at 4° C. After washing, particles were lyophilized.

Particles were compared to Polyethylenimine (PEI), a polycationic polymer used commonly in transfecting mammalian cells with DNA. The first experiment was to compare the toxicity of Ac-DEX particles to PEI polymers. HeLa cells were plated at 40000 cells/well in 96 well plates. Varying concentrations of PEI or Ac-DEX particles are cultured with cells for 4, 8, or 24 hours. After these time points cell viability was measured. HeLa cells grown with Ac-DEX were more viable compared to the cells grown with PEI.

Next, Ac-DEX particles encapsulating a luciferase plasmid were tested for transfection efficiency. Cells were incubated with particles at 5 µg/ml of DNA. Luciferase activity was looked at day 1, 2, 5, 10 and 20 days. Cells were then lysed, proteins were purified and luciferase activity was measured. Ac-DEX particles had somewhat lower activity than the PEI control, but because Ac-DEX particles are less toxic, they are a good candidate for gene delivery.

Example 17

Increased Uptake Using Cell Penetrating Peptides

Cell penetrating peptides (CPP) were used to increase uptake of particles inside non-phagocytic cells. Ac-DEX particles were suspended in PBS at a concentration of 1 mg/mL and aliquots (1.5 mL) were transferred to microcentrifuge tubes. The samples were centrifuged (10,000×g, 15 min) and the supernatant was removed. Using a bath sonicator, the particles were resuspended in a solution (1.5 mL) of aminooxyacetyl-K—(R)$_9$—COOH (10 mg/mL in PBS, pH 7.4). After 2 days at room temperature under gentle agitation, these particles were washed thoroughly. Particles encapsulating plasmid and functionalized with CPP were prepared in the same manner, except the reaction was only allowed to proceed for 1 d. This reaction leads to the formation of oxime linkages between the aminoxy group and the latent aldehydes at the reducing ends of the modified polysaccharide. The use of hydrazides or hydrazines can similarly lead to the formation of acid-labile hydrazone linkages. Additionally, reaction with amines followed by reduction with NaBH$_3$CN or similar reducing agents can lead to amine linkages through reductive amination.

The toxicity of Ac-DEX particles with surface CPPs was tested. HeLa cells were seeded at 40 000 cells per 96 well plate. Two-fold dilutions of particles starting at 1,000 μg/ml with or without CPP on the surface were cultured with HeLa cells. After 24 hours, cells were washed to remove any nonendocytosed particles and allowed to rest for an additional 24 hours. Then a MTT assay was done to measure cell viability. Ac-DEX particles with and without CPP on the surface were not toxic up to 1 000 microgram/ml.

Particles with CPP on the surface were tested for transfection efficiency. Using the method described above, a luciferase plasmid was incorporated inside the particles and tested for efficacy with HeLa cells. CPP on the surface of the Ac-DEX particles statistically increased the level of transfection compared to normal Ac-DEX particles.

Example 18

Chemotherapy for Restenosis

Restenosis typically occurs after angioplasty is done on blood vessels. Restenosis in part is due to an inflammatory response around the site where the angioplasty occurred. Restenosis can be prevented by the treatment with rapamycin and dexamethasone (Zweers et al. (2006) Release of anti-restenosis drugs from poly(ethylene oxide)-poly(DL-lactic-co-glycolic acid) nanoparticles. J Control Release 114:317-24). Ac-DEX particles can encapsulate both rapamycin and dexamethasone using single emulsion techniques or salting methods. Particles can be pegylated as earlier stated.

A HPLC C18 column is used to study the drug loading of rapamycin inside the Ac-DEX particles. Particles are dissolved with acetonitrile, and then injected into the HPLC. Based on a standard curve, the rapamycin content is calculated. While the dexamethasone content is calculated by dissolving approximately 5 mg of Ac-DEX particles in deuterated DMSO and comparing the integral of the dexamethasone peak to the anomeric peak on dextran.

During restenosis, there is an uncontrolled proliferation of smooth muscle cells (SMCs). To test the efficacy of the particles in vitro, smooth muscle cells were enzymatically isolated from the thoracic aortas of adult male Sprague-Dawley rats (6-7 weeks old, approximately 150 g). Cells were plated into 96-well flat-bottom tissue culture plates at a final concentration of 20,000 cells/ml. SMCs were incubated at 37° C. in 5% humidified CO$_2$ with Ac-DEX rapamycin loaded particles at various concentrations. Cell proliferation was induced by mitogenic stimulation with rat platelet-derived growth factor (PDGF, 50 ng/ml). SMC were quantified after 4 days using a MTT assay. Particles loaded with rapamycin have a similar activity compared to nonencapsulated rapamycin.

After in vitro tests, in vivo tests will be done by methods known to those familiar in the art.

Example 19

Drug-Eluting Stents

As described in Example 18, restenosis (an exaggerated neointimal proliferative response) can be triggered in a number of patients following the placement of coronary stents as a treatment for obstructive cardiovascular disease. In order to prevent restenosis, a number of drug-eluting stents have been used (i.e., Randade et al. (2004) Physical characterization of controlled release of paclitaxel from the TAXUS™ Express™ drug-eluting stent. Journal of Biomedical Materials Research Part A 71A:625-634) Restenosis is a result of a number of processes occurring both acutely (i.e., the inflammatory response caused by mechanical injury to the arterial wall secondary to balloon dilation and stent deployment) as well as in the intermediate/long-term (proliferation of SMCs). Due to the multiple processes involved in restenosis, which occur after various periods of time, it is beneficial to control the release rate of drugs from drug-eluting stents (see Venkatraman et al. (2007) Release profiles in drug-eluting stents: Issues and uncertainties. Journal of Controlled Release 120:149-160). Therefore materials such as Ac-DEX, which have easily controlled degradation rates should be promising materials for stent coatings or for the production of fully biodegradable stents.

Using methods known to those familiar in the art, Ac-DEX or other acetal-modified polyhydroxylated polymers can be used to coat metal stents with formulations containing various concentrations of paclitaxel, rapamycin (sirolimus), dexamethasone or any mixture of these drugs. Alternatively, these drugs can be encapsulated in microparticles using techniques such as emulsion/solvent evaporation or nanoprecipitation and the microparticles can be used to coat stents. Additionally, fully biodegradable stents can be made from Ac-DEX using methods known to those familiar in the art. Based on the degree and type of acetal modification, the release rates of drugs from the stents described above can be varied. The drug release profiles from the stents described above are determined by incubating individual stents in medium at 37° C. and pH 7.4. The medium is removed after various time points and analyzed using high performance liquid chromatography (HPLC) to determine the amount of each drug released.

The drug-eluting stents prepared above using Ac-DEX or other acetal-modified polyhydroxylated polymers can be tested in vitro for their ability to reduce proliferation of SMCs using the antiproliferation assay described in Example 18. Following in vitro tests, the stents will be evaluated for their in vivo efficacy using methods known to those familiar in the art.

Example 20

Knockdown of Protein Expression Using Encapsulated siRNA

HeLa-luc cells were seeded (~15,000 cells/well) into each well of a 96-well clear tissue culture plate and allowed to attach overnight in growth medium. Growth medium was composed of DMEM (with phenol red), 10% FBS, and 1% glutamine. Particle samples encapsulating siRNA were prepared at 1000 μg/mL in medium (without antibiotics) by alternately vortexing and sonicating in a Branson 2510 water bath for 20 s to generate homogeneous suspensions. The samples were then serially diluted in medium to give the indicated particle concentrations. Existing medium was replaced with 100 μl of each particle dilution (or medium only) in triplicate wells of each 96-well plate. The cells were allowed to grow for an additional 48 h before being analyzed for gene expression. Lipofectamine 2000 was used as a positive control for siRNA delivery and was prepared according to the manufacturer's instructions. In addition, complexes of DOTAP and siRNA were prepared by mixing DOTAP and siRNA solutions and incubating for 30 min prior to adding to the cells.

The cells of one of the plates were washed with PBS (containing Mg2+ and Ca2+, 3×100 μL), GLO LYSIS Buffer (120 Promega, USA) was added to each well and the plate was incubated at rt. After 20 min, 100 μL from each well was transferred to the wells of a white 96-well tissue culture plate. STEADY-GLO luciferase assay reagent (Promega) was reconstituted according to the manufacturer's instructions and added to each well (100 μL) using an automatic injector. The plate was read using a GLOMAX 96 microplate luminometer (Promega) with a 2 s integration rate.

To determine the total protein content in each well, the cells of a second clear plate were washed as above and lysed with M-PER mammalian protein extraction reagent (50 μl, Pierce-Thermo Fisher, USA) for 20 min at rt. PBS (50 μl) was added to each well, and the plate was briefly vortexed to mix. Samples from each well (50 μl) were added to the wells of a black 96-well tissue culture plate (Corning) already containing PBS (100 μl per well). A solution of 3 mg/mL fluorescamine in acetone (50 μl) was added to each well, and the plate was briefly vortexed to mix. After 5 min, the fluorescence in each well was measured using a plate-reading fluorimeter (excitation=400 nm, emission=460 nm). Protein concentrations were determined using BSA as a standard.

Significant dose dependent knockdown of luciferase production relative to total protein production was found to be caused by siRNA encapsulated in particles but not by free siRNA.

The present examples, methods, procedures, specific compounds and molecules are meant to exemplify and illustrate the invention and should in no way be seen as limiting the scope of the invention. Any patents, publications, publicly available sequences mentioned in this specification are indicative of levels of those skilled in the art to which the invention pertains and are hereby incorporated by reference for all purposes to the same extent as if each was specifically and individually incorporated by reference.

What is claimed is:

1. An acid-degradable modified polyhydroxylated polymer comprising pendant hydroxyl groups, wherein at least 20% of the pendant hydroxyl groups are each directly linked to an acid degradable functional group, wherein the modified polyhydroxylated polymer is insoluble in water.

2. The acid-degradable modified polyhydroxylated polymer of claim 1, wherein each functional group is selected from the group consisting of acetals, aromatic acetals, and ketals.

3. The acid-degradable modified polyhydroxylated polymer of claim 1, wherein the polyhydroxylated polymer is selected from the group consisting of multiply-hydroxylated polymers, polysaccharides, carbohydrates, polyols, polyvinyl alcohol, poly amino acids, polyserine, and 2-(hydroxyethyl)methacrylate.

4. The acid-degradable modified polyhydroxylated polymer of claim 3, wherein the polyhydroxylated polymer is a polysaccharide.

5. The acid-degradable modified polyhydroxylated polymer of claim 4, wherein the polysaccharide is selected from the group consisting of dextran, mannan, pullulan, maltodextrin, starches, cellulose and cellulose derivatives, xanthan gum, locust bean gum, and pectin.

6. The acid-degradable modified polyhydroxylated polymer of claim 5, wherein the polysaccharide is dextran or mannan.

7. The acid-degradable modified polyhydroxylated polymer of claim 1, wherein each acid degradable functional group is an acetal.

8. The acid-degradable modified polyhydroxylated polymer of claim 7, wherein the polyhydroxylated polymer is acetal-derivatized dextran, acetal-derivatized mannan or acetal-derivatized polyvinyl alcohol.

9. The acid-degradable modified polyhydroxylated polymer of claim 1, wherein at least 20% to 85% of the hydroxyl groups in the polyhydroxylated polymer are modified.

10. The acid-degradable modified polyhydroxylated polymer of claim 1, wherein the polymer is in the form of a particle.

11. The acid-degradable modified polyhydroxylated polymer of claim 1, further comprising a bioactive material conjugated or entrapped therein.

12. The acid-degradable modified polyhydroxylated polymer of claim 11, wherein said polymer is in the form of particles, sutures, bulk materials, tissue engineering scaffolds, or implants.

13. The acid-degradable modified polyhydroxylated polymer of claim 11, wherein the bioactive material is selected from the group consisting of polynucleotides, polypeptides, proteins, peptides, antibodies, vaccines, antigens, small molecule drugs, ribonucleotides, amino acids, oligopeptides, peptoids, proteins, plasmid DNA, growth factors and hormones, interleukins, immunostimulatory agents, neurotransmitters, neurostimulatory agents, adrenergic agents, neuromodulatory agents, enzymes, proteases, anticancer agents, antitumor agents, imaging agents, diagnostic agents, antiviral agents, antibacterial agents and therapeutic agents.

14. The acid-degradable modified polyhydroxylated polymer of claim 13, wherein the bioactive material is a polynucleotide.

15. The acid-degradable modified polyhydroxylated polymer of claim 13, wherein the bioactive material is a therapeutic agent.

16. The acid-degradable modified polyhydroxylated polymer of claim 13, wherein the bioactive material is a vaccine.

17. A vaccine composition comprising an acid-degradable modified polyhydroxylated polymer of claim 1, and a bioactive material conjugate or entrapped therein.

18. The composition of claim 17, wherein the bioactive material is selected from the group consisting of polynucleotides, polypeptides, proteins, peptides, antibodies, vaccines, antigens, small molecule drugs, ribonucleotides, amino acids, oligopeptides, peptoids, proteins, plasmid DNA, growth factors and hormones, interleukins, immunostimulatory agents, neurotransmitters, neurostimulatory agents, adrenergic agents, neuromodulatory agents, enzymes, proteases, anticancer agents, antitumor agents, imaging agents, diagnostic agents, antiviral agents, antibacterial agents and therapeutic agents.

19. The composition of claim 17, wherein the bioactive material is a polynucleotide.

20. The composition of claim 17, wherein the bioactive material is a therapeutic agent.

21. A drug-delivery particle comprising an acid-degradable modified polyhydroxylated polymer of claim 1.

22. A method of delivering a bioactive material to a cellular interior, comprising:
contacting the cell with acid-degradable particles comprising a bioactive material bound within or conjugated to an acid-degradable modified polyhydroxylated polymer of claim 1, whereby hydrolysis within an acidic cellular compartment cleaves the acid-degradable functional groups in said modified polyhydroxylated polymer and releases said bioactive material.

* * * * *